US011401337B2

(12) United States Patent
Baliga et al.

(10) Patent No.: US 11,401,337 B2
(45) Date of Patent: Aug. 2, 2022

(54) MODIFIED HUMAN IGM CONSTANT REGIONS FOR MODULATION OF COMPLEMENT-DEPENDENT CYTOLYSIS EFFECTOR FUNCTION

(71) Applicant: IGM Biosciences, Inc., Mountain View, CA (US)

(72) Inventors: Ramesh Baliga, Redwood City, CA (US); Dean Ng, San Francisco, CA (US)

(73) Assignee: IGM Biosciences, Inc., Mountain View, CA (US)

( * ) Notice: Subject to any disclaimer, the term of this patent is extended or adjusted under 35 U.S.C. 154(b) by 59 days.

(21) Appl. No.: 16/500,292

(22) PCT Filed: Apr. 6, 2018

(86) PCT No.: PCT/US2018/026474
§ 371 (c)(1),
(2) Date: Oct. 2, 2019

(87) PCT Pub. No.: WO2018/187702
PCT Pub. Date: Oct. 11, 2018

(65) Prior Publication Data
US 2021/0147567 A1 May 20, 2021

Related U.S. Application Data

(60) Provisional application No. 62/483,087, filed on Apr. 7, 2017.

(51) Int. Cl.
*C07K 16/28* (2006.01)

(52) U.S. Cl.
CPC ...... *C07K 16/2887* (2013.01); *C07K 16/2809* (2013.01); *C07K 2317/31* (2013.01); *C07K 2317/526* (2013.01); *C07K 2317/622* (2013.01); *C07K 2317/71* (2013.01); *C07K 2317/734* (2013.01)

(58) Field of Classification Search
CPC ............ C07K 16/2887; C07K 16/2809; C07K 2317/31; C07K 2317/526; C07K 2317/622; C07K 2317/71; C07K 2317/734; C07K 16/00; A61P 35/00; C12Q 1/68
See application file for complete search history.

(56) References Cited

U.S. PATENT DOCUMENTS

| 5,510,465 | A | 4/1996 | Tsay |
|---|---|---|---|
| 8,377,435 | B2 | 2/2013 | Bhat |
| 9,409,976 | B2 | 8/2016 | Teng |
| 9,458,241 | B2 | 10/2016 | Bhat |
| 9,938,347 | B2 | 4/2018 | Wang |
| 9,951,134 | B2 | 4/2018 | Keyt |
| 10,101,333 | B2 | 10/2018 | Smider |
| 10,351,631 | B2 | 7/2019 | Keyt |
| 10,400,038 | B2 | 9/2019 | Keyt |
| 10,604,559 | B2 | 3/2020 | Carroll |
| 10,618,978 | B2 | 4/2020 | Keyt |
| 10,689,449 | B2 | 6/2020 | Wang |
| 10,954,302 | B2 | 3/2021 | Keyt |
| 10,975,147 | B2 | 4/2021 | Keyt |
| 2012/0316071 | A1* | 12/2012 | Smider ................. C07K 16/00 506/1 |
| 2015/0057437 | A1 | 2/2015 | Takahashi |
| 2015/0071948 | A1* | 3/2015 | Lazar ................. C07K 16/2887 424/178.1 |
| 2016/0368971 | A1 | 12/2016 | Keyt |
| 2018/0009897 | A1 | 1/2018 | Wang |
| 2018/0118814 | A1 | 5/2018 | Carroll |
| 2018/0118816 | A1 | 5/2018 | Keyt |
| 2018/0265596 | A1 | 9/2018 | Keyt |
| 2019/0002566 | A1 | 1/2019 | Keyt |
| 2019/0100597 | A1 | 4/2019 | Keyt |
| 2019/0185570 | A1 | 6/2019 | Keyt |
| 2019/0330360 | A1 | 10/2019 | Wang |
| 2019/0330374 | A1 | 10/2019 | Wang |
| 2019/0338031 | A1 | 11/2019 | Keyt |
| 2019/0338040 | A1 | 11/2019 | Keyt |
| 2019/0338041 | A1 | 11/2019 | Baliga |
| 2020/0190190 | A1 | 6/2020 | Keyt |
| 2021/0032357 | A1 | 2/2021 | Keyt |
| 2021/0087273 | A1 | 3/2021 | Baliga |
| 2021/0163600 | A1 | 6/2021 | Keyt |

(Continued)

FOREIGN PATENT DOCUMENTS

| JP | H4221321 | 8/1992 |
|---|---|---|
| JP | 2013510164 | 3/2013 |

(Continued)

OTHER PUBLICATIONS

Lund et al. (The Journal of Immunology 157:4963-4969 (Year: 1996).*
Edwards et al., J Mol Biol. Nov. 14, 2003;334(1): 103-118 (Year: 2003).*
Wu et al., J. Mol. Biol. 294: 151-162 (Year: 1999).*
Lloyd et al., Protein Engineering, Design & Selection 22:159-168 (Year: 2009).*
Yu et al., Investigative Ophthalmology & Visual Science 49(2): 522-527 (Year: 2008).*
Rudikoff et al., Proc. Natl. Acad. Sci. USA, 79:1979-1983 (Year: 1982).*

(Continued)

*Primary Examiner* — Phuong Huynh

(57) ABSTRACT

The disclosure provides modified human IgM heavy chain constant regions that include one or more amino acid substitutions, e.g., in the Cμ3 domain, where a modified human IgM antibody comprising the modified IgM constant region and a heavy chain variable region specific for a target antigen exhibits reduced complement-dependent cytotoxicity (CDC) of cells expressing the target antigen relative to a corresponding wild-type human IgM antibody.

36 Claims, 9 Drawing Sheets

Specification includes a Sequence Listing.

(56) References Cited

U.S. PATENT DOCUMENTS

| | | |
|---|---|---|
| 2021/0380701 A1 | 12/2021 | Baliga |
| 2021/0388098 A1 | 12/2021 | Keyt |

FOREIGN PATENT DOCUMENTS

| | | | |
|---|---|---|---|
| WO | WO-03074679 A2 * | 9/2003 | ............. C07K 16/00 |
| WO | 2004110143 | 12/2004 | |
| WO | 2006052641 | 5/2006 | |
| WO | 2013120012 | 8/2013 | |
| WO | 2015053887 | 4/2015 | |
| WO | 2015120474 | 8/2015 | |
| WO | 2015129651 | 9/2015 | |
| WO | 2015153912 | 10/2015 | |
| WO | 2016118641 | 7/2016 | |
| WO | 2016141303 | 9/2016 | |
| WO | 2016154593 | 9/2016 | |
| WO | 2016168758 | 10/2016 | |
| WO | 2017059380 | 4/2017 | |
| WO | 2017059387 | 4/2017 | |
| WO | 2017196867 | 11/2017 | |
| WO | 2018017761 | 1/2018 | |
| WO | 2018017763 | 1/2018 | |
| WO | 2018017888 | 1/2018 | |
| WO | 2018017889 | 1/2018 | |
| WO | 2019165340 | 8/2019 | |
| WO | 2019169314 | 9/2019 | |
| WO | 2020086745 | 4/2020 | |

OTHER PUBLICATIONS

Written Opinion dated Jun. 8, 2018 issued in PCT Patent Application No. PCT/US2018/026474.
Arya, S., et al., (1994), "Mapping of amino acid residues in the C mu 3 domain of mouse IgM important in macromolecular assembly and complement-dependent cytolysis", The Journal of Immunology, vol. 152: 1206-1212.
Wright, J., et al., (1990), "C1 binding by mouse IgM. The effect of abnormal glycosylation at position 402 resulting from a serine to asparagine exchange at residue 406 of the μ-chain", The Journal of Biological Chemistry, vol. 265(18) 10506-10513.
Wright, J., et al., (1988), "C1 binding by murine IgM. The effect of a Pro-to-Ser exchange at residue 436 of the μ-chain". The Journal of Biological Chemistry, vol. 265(18): 10506-10513.
Hezareh, M., et al., (2001), "Effector Function Activities of a Panel of Mutants of a Broadly Neutralizing Antibody against Human Immunodeficiency Virus Type 1", Journal of Virology, 75(24): 12161-12168.
Idusogie, E., et al., (2000), "Mapping of the C1q Binding Site on Rituxan, a Chimeric Antibody with a Human IgG1 Fc" The Journal of Immunology, 164(8): 4178-4184.
Keyt, A., et al., (2020), "Structure, Function, and Therapeutic Use of IgM Antibodies", Antibodies, 9: 53; doi: 10.3390/antib9040053, 35 pages.
Taylor, B., et al., (1994), "C1q binding properties of monomer and polymer forms of mouse IgM μ-chain variants. Pro544Gly and Pro434ala.", Journal of Immunology, 153: 5303-5313.
Wright, F., et al., (1988), "C1 Binding by Murine IgM", The Journal of Biological Chemistry, 263(23):11221-11226.
Brüggemann M., et al., (1987), "Comparison of the effector functions of human immunoglobulins using a matched set of chimeric antibodies", J. Exp. Med, 166: 1351-1361.
Castro, C., et al., (2014), "Putting J chain back on the map: how might its expression define plasma cell development?", The Journal of Immunology, 193: 3248-3255.
Collins, C., et al., (2002), "Differential activation of human and guinea pig complement by pentameric and hexameric IgM", Eur J. Immunol. 32(6): 1802-1810.
Duramad, O., et al., (2014), "IGM-55.5 a novel monoclonal human recombinant IgM antibody with potent activity against B cell leukemia and lymphoma" IGM Biosciences, Inc.—Research and Development SRI International—Cancer Pharmacology, Stanford—Department of Obstetrics and Gynecology, Abstract No. 645 AACR Annual Meeting, Apr. 5-9, 2014, San Diego CA.
Hensel, F., et al., (2013), "Early development of PAT-SM6 for the treatment of melanoma", 23(4): 264-275.
Pawluczkowycz, A., et al., (2009), "Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX", The Journal of Immunology, 183: 749-458.
Perkins, S., et al., (1991), "Solution Structure of Human and Mouse Immunoglobulin M by Synchrotron X-ray Scattering and Molecular Graphics Modelling, A Possible Mechanism for Complement Activation", J. Mol Biol, 221: 1345-1366.
Rasche, L., et al., (2015), "GRP78-directed immunotherapy in relapsed or refractory multiple myeloma—results from a phase 1 trial with the monoclonal immunoglobulin M antibody PAT-SM6", Haematologica, J. Mol. Biol, 100(3): 377-384.
Sharp, T., et al., (2019), "Insights into IgM-mediated complement activation based on in situ structures of IgM-C1-C4b", Proc Natl. Acad Sci USA, 116(24): 11900-11905.
Shulman, M., et al., (1987), "Complement activation by IgM: evidence for the importance of the third constant domain of the μ heavy chain", Eur. J. Immunol, 17: 549-554.
Sørman A., et al., (2014), "How antibodies use complement to regulate antibody responses", Mol Immunol, 61, 79-88.
Sørman, A. et al., (2017), "IgM is Unable to Enhance Antibody Responses in Mice Lacking C1q or C3", Scand J Immunol, 85: 381-382.
Wibroe, P., et al., (2014), "The Role of complement in Antibody Therapy for Infectious Diseases", Microbiology Spectrum 2(2): AID-0015-2014, 9 pages.
Shulman, M., et al., (1986), "Activation of complement by immunoglobulin M is impaired by the substitution serine-406—asparagine in the immunoglobulin mu heavy chain", Proc. Natl. Acad. Sci USA, 83: 7678-7682.

* cited by examiner 1. 1.5.3 IgM V15J
2. 1.5.3 IgM V15J P311A
3. 1.5.3 IgM V15J P313S
4. 1.5.3 IgM V15J P311A P313S

| | HillSlope | IC50 |
|---|---|---|
| P311A | 1.4 | 31 nM |
| P313S | 1.5 | 16 nM |
| P311A P313S | 1.3 | 29 nM |

SEQUENCE LISTING

<160> NUMBER OF SEQ ID NOS: 40

<210> SEQ ID NO 1
<211> LENGTH: 453
<212> TYPE: PRT
<213> ORGANISM: Homo sapiens

<400> SEQUENCE: 1

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255
```

```
Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Arg Phe Thr Cys Thr
        290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
            435                 440                 445

Ala Gly Thr Cys Tyr
    450

<210> SEQ ID NO 2
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
```

```
                145                 150                 155                 160
        Thr Asp Gln Val Gln Ala Glu Ala Lys Glu Ser Gly Pro Thr Thr Tyr
                        165                 170                 175

Lys Val Thr Ser Thr Leu Thr Ile Lys Glu Ser Asp Trp Leu Ser Gln
                        180                 185                 190

Ser Met Phe Thr Cys Arg Val Asp His Arg Gly Leu Thr Phe Gln Gln
                        195                 200                 205

Asn Ala Ser Ser Met Cys Val Pro Asp Gln Asp Thr Ala Ile Arg Val
                        210                 215                 220

Phe Ala Ile Pro Pro Ser Phe Ala Ser Ile Phe Leu Thr Lys Ser Thr
        225                 230                 235                 240

Lys Leu Thr Cys Leu Val Thr Asp Leu Thr Thr Tyr Asp Ser Val Thr
                        245                 250                 255

Ile Ser Trp Thr Arg Gln Asn Gly Glu Ala Val Lys Thr His Thr Asn
                        260                 265                 270

Ile Ser Glu Ser His Pro Asn Ala Thr Phe Ser Ala Val Gly Glu Ala
                        275                 280                 285

Ser Ile Cys Glu Asp Asp Trp Asn Ser Gly Glu Arg Phe Thr Cys Thr
                        290                 295                 300

Val Thr His Thr Asp Leu Ala Ser Pro Leu Lys Gln Thr Ile Ser Arg
        305                 310                 315                 320

Pro Lys Gly Val Ala Leu His Arg Pro Asp Val Tyr Leu Leu Pro Pro
                        325                 330                 335

Ala Arg Glu Gln Leu Asn Leu Arg Glu Ser Ala Thr Ile Thr Cys Leu
                        340                 345                 350

Val Thr Gly Phe Ser Pro Ala Asp Val Phe Val Gln Trp Met Gln Arg
                        355                 360                 365

Gly Gln Pro Leu Ser Pro Glu Lys Tyr Val Thr Ser Ala Pro Met Pro
                        370                 375                 380

Glu Pro Gln Ala Pro Gly Arg Tyr Phe Ala His Ser Ile Leu Thr Val
        385                 390                 395                 400

Ser Glu Glu Glu Trp Asn Thr Gly Glu Thr Tyr Thr Cys Val Val Ala
                        405                 410                 415

His Glu Ala Leu Pro Asn Arg Val Thr Glu Arg Thr Val Asp Lys Ser
                        420                 425                 430

Thr Gly Lys Pro Thr Leu Tyr Asn Val Ser Leu Val Met Ser Asp Thr
                        435                 440                 445

Ala Gly Thr Cys Tyr
                        450

<210> SEQ ID NO 3
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
                35                  40                  45
```

-continued

```
Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
                115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
                180                 185                 190

Ser Met Phe Thr Cys Arg Val Asp His Arg Gly Leu Thr Phe Gln Gln
                195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
                260                 265                 270

Ile Ser Glu Ser His Pro Asn Ala Thr Phe Ser Ala Val Gly Glu Ala
                275                 280                 285

Ser Ile Cys Glu Asp Asp Trp Asn Ser Gly Glu Arg Phe Thr Cys Thr
                290                 295                 300

Val Thr His Thr Asp Leu Pro Ser Ser Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
                355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
                435                 440                 445

Ala Gly Thr Cys Tyr
450
```

-continued

```
<210> SEQ ID NO 4
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
290                 295                 300

Val Thr His Thr Asp Leu Ala Ser Ser Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365
```

```
Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
            435                 440                 445

Ala Gly Thr Cys Tyr
        450

<210> SEQ ID NO 5
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270
```

```
Ile Ser Glu Ser His Pro Asn Ala Thr Phe Ser Ala Val Gly Glu Ala
            275                 280                 285

Ser Ile Cys Glu Asp Gly Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
                355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
                435                 440                 445

Ala Gly Thr Cys Tyr
            450

<210> SEQ ID NO 6
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
```

```
                165                 170                 175
Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Asn Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 7
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Ile Ile Val Pro
    50                  55                  60
```

```
Leu Asn Asn Arg Glu Asn Ile Ser Asp Pro Thr Ser Pro Leu Arg Thr
 65                  70                  75                  80

Arg Phe Val Tyr His Leu Ser Asp Leu Cys Lys Lys Cys Asp Pro Thr
                 85                  90                  95

Glu Val Glu Leu Asp Asn Gln Ile Val Thr Ala Thr Gln Ser Asn Ile
            100                 105                 110

Cys Asp Glu Asp Ser Ala Thr Glu Thr Cys Tyr Thr Tyr Asp Arg Asn
            115                 120                 125

Lys Cys Tyr Thr Ala Val Val Pro Leu Val Tyr Gly Gly Glu Thr Lys
130                 135                 140

Met Val Glu Thr Ala Leu Thr Pro Asp Ala Cys Tyr Pro Asp
145                 150                 155

<210> SEQ ID NO 8
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Trp Ser Tyr Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Ile Ser Tyr Thr Met His Trp Val Arg Gln Ala Pro Gly Gln Gly Leu
 50                  55                  60

Glu Trp Met Gly Tyr Ile Asn Pro Arg Ser Gly Tyr Thr His Tyr Asn
 65                  70                  75                  80

Gln Lys Leu Lys Asp Lys Ala Thr Leu Thr Ala Asp Lys Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg Ser Ala Tyr Tyr Asp Tyr Asp Gly Phe Ala Tyr
            115                 120                 125

Trp Gly Gln Gly Thr Leu Val Thr Val Ser Ser Gly Gly Gly Gly Ser
        130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Ser Ala Ser Ser Val Ser Tyr Met Asn Trp Tyr Gln Gln Lys
            180                 185                 190

Pro Gly Lys Ala Pro Lys Arg Leu Ile Tyr Asp Thr Ser Lys Leu Ala
            195                 200                 205

Ser Gly Val Pro Ser Arg Phe Ser Gly Ser Gly Ser Gly Thr Asp Phe
        210                 215                 220

Thr Leu Thr Ile Ser Ser Leu Gln Pro Glu Asp Phe Ala Thr Tyr Tyr
225                 230                 235                 240

Cys Gln Gln Trp Ser Ser Asn Pro Pro Thr Phe Gly Gly Gly Thr Lys
                245                 250                 255

Leu Glu Ile Lys Gly Gly Gly Gly Ser Gly Gly Gly Gly Ser Gly Gly
            260                 265                 270
```

```
Gly Gly Ser Gln Glu Asp Glu Arg Ile Val Leu Val Asp Asn Lys Cys
            275                 280                 285

Lys Cys Ala Arg Ile Thr Ser Arg Ile Ile Arg Ser Ser Glu Asp Pro
    290                 295                 300

Asn Glu Asp Ile Val Glu Arg Asn Ile Arg Ile Ile Val Pro Leu Asn
305                 310                 315                 320

Asn Arg Glu Asn Ile Ser Asp Pro Thr Ser Pro Leu Arg Thr Arg Phe
                325                 330                 335

Val Tyr His Leu Ser Asp Leu Cys Lys Lys Cys Asp Pro Thr Glu Val
            340                 345                 350

Glu Leu Asp Asn Gln Ile Val Thr Ala Thr Gln Ser Asn Ile Cys Asp
            355                 360                 365

Glu Asp Ser Ala Thr Glu Thr Cys Tyr Thr Tyr Asp Arg Asn Lys Cys
370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp
                405                 410

<210> SEQ ID NO 9
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
```

```
                  210                 215                 220
Trp Ser Ser Asn Pro Pro Thr Phe Gly Gly Gly Thr Lys Leu Glu Ile
225                 230                 235                 240

Lys Gly Gly Gly Ser Gly Gly Gly Ser Gly Gly Gly Gly Ser
                245                 250                 255

Gln Glu Asp Glu Arg Ile Val Leu Val Asp Asn Lys Cys Lys Cys Ala
                260                 265                 270

Arg Ile Thr Ser Arg Ile Ile Arg Ser Ser Glu Asp Pro Asn Glu Asp
                275                 280                 285

Ile Val Glu Arg Asn Ile Arg Ile Ile Val Pro Leu Asn Asn Arg Glu
                290                 295                 300

Asn Ile Ser Asp Pro Thr Ser Pro Leu Arg Thr Arg Phe Val Tyr His
305                 310                 315                 320

Leu Ser Asp Leu Cys Lys Lys Cys Asp Pro Thr Glu Val Glu Leu Asp
                325                 330                 335

Asn Gln Ile Val Thr Ala Thr Gln Ser Asn Ile Cys Asp Glu Asp Ser
                340                 345                 350

Ala Thr Glu Thr Cys Tyr Thr Tyr Asp Arg Asn Lys Cys Tyr Thr Ala
                355                 360                 365

Val Val Pro Leu Val Tyr Gly Gly Glu Thr Lys Met Val Glu Thr Ala
370                 375                 380

Leu Thr Pro Asp Ala Cys Tyr Pro Asp
385                 390

<210> SEQ ID NO 10
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
                35                  40                  45

Glu Asp Pro Asn Glu Asp Ile Val Glu Arg Asn Ile Arg Ile Ile Val
                50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
                100                 105                 110

Ile Cys Asp Glu Asp Ser Ala Thr Glu Thr Cys Tyr Thr Tyr Asp Arg
                115                 120                 125

Asn Lys Cys Tyr Thr Ala Val Val Pro Leu Val Tyr Gly Gly Glu Thr
                130                 135                 140

Lys Met Val Glu Thr Ala Leu Thr Pro Asp Ala Cys Tyr Pro Asp Gly
145                 150                 155                 160

Gly Gly Gly Ser Gly Gly Gly Ser Gly Gly Gly Ser Gln Val
                165                 170                 175
```

Gln Leu Val Gln Ser Gly Ala Glu Val Lys Lys Pro Gly Ala Ser Val
                180                 185                 190

Lys Val Ser Cys Lys Ala Ser Gly Tyr Thr Phe Ile Ser Tyr Thr Met
            195                 200                 205

His Trp Val Arg Gln Ala Pro Gly Gln Gly Leu Glu Trp Met Gly Tyr
        210                 215                 220

Ile Asn Pro Arg Ser Gly Tyr Thr His Tyr Asn Gln Lys Leu Lys Asp
225                 230                 235                 240

Lys Ala Thr Leu Thr Ala Asp Lys Ser Ala Ser Thr Ala Tyr Met Glu
                245                 250                 255

Leu Ser Ser Leu Arg Ser Glu Asp Thr Ala Val Tyr Tyr Cys Ala Arg
            260                 265                 270

Ser Ala Tyr Tyr Asp Tyr Asp Gly Phe Ala Tyr Trp Gly Gln Gly Thr
        275                 280                 285

Leu Val Thr Val Ser Ser Gly Gly Gly Gly Ser Gly Gly Gly Gly Ser
        290                 295                 300

Gly Gly Gly Gly Ser Asp Ile Gln Met Thr Gln Ser Pro Ser Ser Leu
305                 310                 315                 320

Ser Ala Ser Val Gly Asp Arg Val Thr Ile Thr Cys Ser Ala Ser Ser
                325                 330                 335

Ser Val Ser Tyr Met Asn Trp Tyr Gln Gln Lys Pro Gly Lys Ala Pro
            340                 345                 350

Lys Arg Leu Ile Tyr Asp Thr Ser Lys Leu Ala Ser Gly Val Pro Ser
        355                 360                 365

Arg Phe Ser Gly Ser Gly Ser Gly Thr Asp Phe Thr Leu Thr Ile Ser
        370                 375                 380

Ser Leu Gln Pro Glu Asp Phe Ala Thr Tyr Tyr Cys Gln Gln Trp Ser
385                 390                 395                 400

Ser Asn Pro Pro Thr Phe Gly Gly Gly Thr Lys Leu Glu Ile Lys
                405                 410                 415

<210> SEQ ID NO 11
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Glu Asp Glu Arg Ile Val Leu Val Asp Asn Lys Cys Lys Cys Ala
1               5                   10                  15

Arg Ile Thr Ser Arg Ile Arg Ser Ser Glu Asp Pro Asn Glu Asp
            20                  25                  30

Ile Val Glu Arg Asn Ile Arg Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

-continued

Leu Thr Pro Asp Ala Cys Tyr Pro Asp Gly Gly Gly Ser Gly Gly
    130                 135                 140

Gly Gly Ser Gly Gly Gly Ser Gln Val Gln Leu Val Gln Ser Gly
145                 150                 155                 160

Ala Glu Val Lys Lys Pro Gly Ala Ser Val Lys Val Ser Cys Lys Ala
                165                 170                 175

Ser Gly Tyr Thr Phe Ile Ser Tyr Thr Met His Trp Val Arg Gln Ala
            180                 185                 190

Pro Gly Gln Gly Leu Glu Trp Met Gly Tyr Ile Asn Pro Arg Ser Gly
        195                 200                 205

Tyr Thr His Tyr Asn Gln Lys Leu Lys Asp Lys Ala Thr Leu Thr Ala
    210                 215                 220

Asp Lys Ser Ala Ser Thr Ala Tyr Met Glu Leu Ser Ser Leu Arg Ser
225                 230                 235                 240

Glu Asp Thr Ala Val Tyr Tyr Cys Ala Arg Ser Ala Tyr Tyr Asp Tyr
                245                 250                 255

Asp Gly Phe Ala Tyr Trp Gly Gln Gly Thr Leu Val Thr Val Ser Ser
            260                 265                 270

Gly Gly Gly Gly Ser Gly Gly Gly Ser Gly Gly Gly Gly Ser Asp
        275                 280                 285

Ile Gln Met Thr Gln Ser Pro Ser Ser Leu Ser Ala Ser Val Gly Asp
    290                 295                 300

Arg Val Thr Ile Thr Cys Ser Ala Ser Ser Val Ser Tyr Met Asn
305                 310                 315                 320

Trp Tyr Gln Gln Lys Pro Gly Lys Ala Pro Lys Arg Leu Ile Tyr Asp
                325                 330                 335

Thr Ser Lys Leu Ala Ser Gly Val Pro Ser Arg Phe Ser Gly Ser Gly
            340                 345                 350

Ser Gly Thr Asp Phe Thr Leu Thr Ile Ser Ser Leu Gln Pro Glu Asp
        355                 360                 365

Phe Ala Thr Tyr Tyr Cys Gln Gln Trp Ser Ser Asn Pro Pro Thr Phe
    370                 375                 380

Gly Gly Gly Thr Lys Leu Glu Ile Lys
385                 390

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser Gly Gly Gly Ser Gly Gly Gly Gly Ser
1               5                   10                  15

<210> SEQ ID NO 13
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Gln Ser Gly Ala Glu Val Lys Lys Pro Gly Glu
1               5                   10                  15

```
Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ser Tyr Gly Ser Gly Ser Pro Asn Phe Asp Tyr Trp
            100                 105                 110

Gly Gln Gly Thr Leu Val Thr Val Ser Ser
        115                 120

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

<210> SEQ ID NO 15
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80
```

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Ala Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 16
<211> LENGTH: 453
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 16

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

-continued

```
Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 17
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
```

```
                290                 295                 300
Val Thr His Thr Asp Ala Pro Ser Pro Leu Ala Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
                355                 360                 365

Gly Gln Pro Leu Ser Pro Glu Lys Tyr Val Thr Ser Ala Pro Met Pro
                370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
                435                 440                 445

Ala Gly Thr Cys Tyr
    450

<210> SEQ ID NO 18
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
                35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
                115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
                180                 185                 190
```

```
Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
        210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
        290                 295                 300

Val Thr His Thr Asp Ser Pro Ser Pro Leu Ser Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
        370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 19
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95
```

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Ala Ala Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 20
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gly Ser Ala Ser Ala Pro Thr Leu Phe Pro Leu Val Ser Cys Glu Asn
1               5                   10                  15
Ser Pro Ser Asp Thr Ser Ser Val Ala Val Gly Cys Leu Ala Gln Asp
            20                  25                  30
Phe Leu Pro Asp Ser Ile Thr Phe Ser Trp Lys Tyr Lys Asn Asn Ser
        35                  40                  45
Asp Ile Ser Ser Thr Arg Gly Phe Pro Ser Val Leu Arg Gly Gly Lys
    50                  55                  60
Tyr Ala Ala Thr Ser Gln Val Leu Leu Pro Ser Lys Asp Val Met Gln
65                  70                  75                  80
Gly Thr Asp Glu His Val Val Cys Lys Val Gln His Pro Asn Gly Asn
                85                  90                  95
Lys Glu Lys Asn Val Pro Leu Pro Val Ile Ala Glu Leu Pro Pro Lys
            100                 105                 110
Val Ser Val Phe Val Pro Pro Arg Asp Gly Phe Phe Gly Asn Pro Arg
        115                 120                 125
Lys Ser Lys Leu Ile Cys Gln Ala Thr Gly Phe Ser Pro Arg Gln Ile
    130                 135                 140
Gln Val Ser Trp Leu Arg Glu Gly Lys Gln Val Gly Ser Gly Val Thr
145                 150                 155                 160
Thr Asp Gln Val Gln Ala Glu Ala Lys Glu Ser Gly Pro Thr Thr Tyr
                165                 170                 175
Lys Val Thr Ser Thr Leu Thr Ile Lys Glu Ser Asp Trp Leu Ser Gln
            180                 185                 190
Ser Met Phe Thr Cys Arg Val Asp His Arg Gly Leu Thr Phe Gln Gln
        195                 200                 205
Asn Ala Ser Ser Met Cys Val Pro Asp Gln Asp Thr Ala Ile Arg Val
    210                 215                 220
Phe Ala Ile Pro Pro Ser Phe Ala Ser Ile Phe Leu Thr Lys Ser Thr
225                 230                 235                 240
Lys Leu Thr Cys Leu Val Thr Asp Leu Thr Thr Tyr Asp Ser Val Thr
                245                 250                 255
Ile Ser Trp Thr Arg Gln Asn Gly Glu Ala Val Lys Thr His Thr Asn
            260                 265                 270
Ile Ser Glu Ser His Pro Asn Ala Thr Phe Ser Ala Val Gly Glu Ala
        275                 280                 285
Ser Ile Cys Glu Asp Asp Trp Asn Ser Gly Glu Arg Phe Thr Cys Thr
    290                 295                 300
Val Thr His Thr Asp Ala Pro Ser Ser Leu Lys Gln Thr Ile Ser Arg
305                 310                 315                 320
Pro Lys Gly Val Ala Leu His Arg Pro Asp Val Tyr Leu Leu Pro Pro
                325                 330                 335
Ala Arg Glu Gln Leu Asn Leu Arg Glu Ser Ala Thr Ile Thr Cys Leu
            340                 345                 350
Val Thr Gly Phe Ser Pro Ala Asp Val Phe Val Gln Trp Met Gln Arg
        355                 360                 365
Gly Gln Pro Leu Ser Pro Glu Lys Tyr Val Thr Ser Ala Pro Met Pro
    370                 375                 380
Glu Pro Gln Ala Pro Gly Arg Tyr Phe Ala His Ser Ile Leu Thr Val
385                 390                 395                 400
Ser Glu Glu Glu Trp Asn Thr Gly Glu Thr Tyr Thr Cys Val Val Ala
                405                 410                 415
```

```
His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
            435                 440                 445

Ala Gly Thr Cys Tyr
        450

<210> SEQ ID NO 21
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Ala Ser Pro Leu Ala Gln Thr Ile Ser Arg
```

```
                305                 310                 315                 320
        Pro Lys Gly Val Ala Leu His Arg Pro Asp Val Tyr Leu Leu Pro Pro
                        325                 330                 335

Ala Arg Glu Gln Leu Asn Leu Arg Glu Ser Ala Thr Ile Thr Cys Leu
                        340                 345                 350

Val Thr Gly Phe Ser Pro Ala Asp Val Phe Val Gln Trp Met Gln Arg
                        355                 360                 365

Gly Gln Pro Leu Ser Pro Glu Lys Tyr Val Thr Ser Ala Pro Met Pro
                        370                 375                 380

Glu Pro Gln Ala Pro Gly Arg Tyr Phe Ala His Ser Ile Leu Thr Val
        385                 390                 395                 400

Ser Glu Glu Glu Trp Asn Thr Gly Glu Thr Tyr Thr Cys Val Val Ala
                        405                 410                 415

His Glu Ala Leu Pro Asn Arg Val Thr Glu Arg Thr Val Asp Lys Ser
                        420                 425                 430

Thr Gly Lys Pro Thr Leu Tyr Asn Val Ser Leu Val Met Ser Asp Thr
                        435                 440                 445

Ala Gly Thr Cys Tyr
                        450

<210> SEQ ID NO 22
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Ser Ala Ser Ala Pro Thr Leu Phe Pro Leu Val Ser Cys Glu Asn
        1               5                   10                  15

Ser Pro Ser Asp Thr Ser Ser Val Ala Val Gly Cys Leu Ala Gln Asp
                        20                  25                  30

Phe Leu Pro Asp Ser Ile Thr Phe Ser Trp Lys Tyr Lys Asn Asn Ser
                        35                  40                  45

Asp Ile Ser Ser Thr Arg Gly Phe Pro Ser Val Leu Arg Gly Gly Lys
                50                  55                  60

Tyr Ala Ala Thr Ser Gln Val Leu Leu Pro Ser Lys Asp Val Met Gln
        65                  70                  75                  80

Gly Thr Asp Glu His Val Val Cys Lys Val Gln His Pro Asn Gly Asn
                        85                  90                  95

Lys Glu Lys Asn Val Pro Leu Pro Val Ile Ala Glu Leu Pro Pro Lys
                        100                 105                 110

Val Ser Val Phe Val Pro Pro Arg Asp Gly Phe Phe Gly Asn Pro Arg
                        115                 120                 125

Lys Ser Lys Leu Ile Cys Gln Ala Thr Gly Phe Ser Pro Arg Gln Ile
                130                 135                 140

Gln Val Ser Trp Leu Arg Glu Gly Lys Gln Val Gly Ser Gly Val Thr
        145                 150                 155                 160

Thr Asp Gln Val Gln Ala Glu Ala Lys Glu Ser Gly Pro Thr Thr Tyr
                        165                 170                 175

Lys Val Thr Ser Thr Leu Thr Ile Lys Glu Ser Asp Trp Leu Ser Gln
                        180                 185                 190

Ser Met Phe Thr Cys Arg Val Asp His Arg Gly Leu Thr Phe Gln Gln
                        195                 200                 205
```

```
Asn Ala Ser Ser Met Cys Val Pro Asp Gln Asp Thr Ala Ile Arg Val
    210                 215                 220
Phe Ala Ile Pro Pro Ser Phe Ala Ser Ile Phe Leu Thr Lys Ser Thr
225                 230                 235                 240
Lys Leu Thr Cys Leu Val Thr Asp Leu Thr Thr Tyr Asp Ser Val Thr
                245                 250                 255
Ile Ser Trp Thr Arg Gln Asn Gly Glu Ala Val Lys Thr His Thr Asn
            260                 265                 270
Ile Ser Glu Ser His Pro Asn Ala Thr Phe Ser Ala Val Gly Glu Ala
        275                 280                 285
Ser Ile Cys Glu Asp Asp Trp Asn Ser Gly Arg Phe Thr Cys Thr
    290                 295                 300
Val Thr His Thr Asp Leu Pro Ser Ser Leu Ala Gln Thr Ile Ser Arg
305                 310                 315                 320
Pro Lys Gly Val Ala Leu His Arg Pro Asp Val Tyr Leu Leu Pro Pro
                325                 330                 335
Ala Arg Glu Gln Leu Asn Leu Arg Glu Ser Ala Thr Ile Thr Cys Leu
            340                 345                 350
Val Thr Gly Phe Ser Pro Ala Asp Val Phe Val Gln Trp Met Gln Arg
        355                 360                 365
Gly Gln Pro Leu Ser Pro Glu Lys Tyr Val Thr Ser Ala Pro Met Pro
    370                 375                 380
Glu Pro Gln Ala Pro Gly Arg Tyr Phe Ala His Ser Ile Leu Thr Val
385                 390                 395                 400
Ser Glu Glu Glu Trp Asn Thr Gly Glu Thr Tyr Thr Cys Val Val Ala
                405                 410                 415
His Glu Ala Leu Pro Asn Arg Val Thr Glu Arg Thr Val Asp Lys Ser
            420                 425                 430
Thr Gly Lys Pro Thr Leu Tyr Asn Val Ser Leu Val Met Ser Asp Thr
        435                 440                 445
Ala Gly Thr Cys Tyr
    450

<210> SEQ ID NO 23
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Ser Ala Ser Ala Pro Thr Leu Phe Pro Leu Val Ser Cys Glu Asn
1               5                   10                  15
Ser Pro Ser Asp Thr Ser Ser Val Ala Val Gly Cys Leu Ala Gln Asp
            20                  25                  30
Phe Leu Pro Asp Ser Ile Thr Phe Ser Trp Lys Tyr Lys Asn Asn Ser
        35                  40                  45
Asp Ile Ser Ser Thr Arg Gly Phe Pro Ser Val Leu Arg Gly Gly Lys
    50                  55                  60
Tyr Ala Ala Thr Ser Gln Val Leu Leu Pro Ser Lys Asp Val Met Gln
65                  70                  75                  80
Gly Thr Asp Glu His Val Val Cys Lys Val Gln His Pro Asn Gly Asn
                85                  90                  95
Lys Glu Lys Asn Val Pro Leu Pro Val Ile Ala Glu Leu Pro Pro Lys
            100                 105                 110
```

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
        130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Asp Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
        435                 440                 445

Ala Gly Thr Cys Tyr
    450

<210> SEQ ID NO 24
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Ser Ala Ser Ala Pro Thr Leu Phe Pro Leu Val Ser Cys Glu Asn

```
  1               5                  10                 15
Ser Pro Ser Asp Thr Ser Ser Val Ala Val Gly Cys Leu Ala Gln Asp
                20                  25                 30

Phe Leu Pro Asp Ser Ile Thr Phe Ser Trp Lys Tyr Lys Asn Asn Ser
                35                  40                 45

Asp Ile Ser Ser Thr Arg Gly Phe Pro Ser Val Leu Arg Gly Gly Lys
50                      55                  60

Tyr Ala Ala Thr Ser Gln Val Leu Leu Pro Ser Lys Asp Val Met Gln
65                      70                  75                 80

Gly Thr Asp Glu His Val Val Cys Lys Val Gln His Pro Asn Gly Asn
                85                  90                 95

Lys Glu Lys Asn Val Pro Leu Pro Val Ile Ala Glu Leu Pro Pro Lys
                100                 105                110

Val Ser Val Phe Val Pro Pro Arg Asp Gly Phe Phe Gly Asn Pro Arg
                115                 120                125

Lys Ser Lys Leu Ile Cys Gln Ala Thr Gly Phe Ser Pro Arg Gln Ile
                130                 135                140

Gln Val Ser Trp Leu Arg Glu Gly Lys Gln Val Gly Ser Gly Val Thr
145                     150                 155                160

Thr Asp Gln Val Gln Ala Glu Ala Lys Glu Ser Gly Pro Thr Thr Tyr
                165                 170                175

Lys Val Thr Ser Thr Leu Thr Ile Lys Glu Ser Asp Trp Leu Ser Gln
                180                 185                190

Ser Met Phe Thr Cys Arg Val Asp His Arg Gly Leu Thr Phe Gln Gln
                195                 200                205

Asn Ala Ser Ser Met Cys Val Pro Asp Gln Asp Thr Ala Ile Arg Val
                210                 215                220

Phe Ala Ile Pro Pro Ser Phe Ala Ser Ile Phe Leu Thr Lys Ser Thr
225                     230                 235                240

Lys Leu Thr Cys Leu Val Thr Asp Leu Thr Thr Tyr Asp Ser Val Thr
                245                 250                255

Ile Ser Trp Thr Arg Gln Asn Gly Glu Ala Val Lys Thr His Thr Asn
                260                 265                270

Ile Ser Glu Ser His Pro Asn Ala Thr Phe Ser Ala Val Gly Glu Ala
                275                 280                285

Ser Ile Cys Glu Asp Asp Trp Asn Ser Gly Glu Arg Phe Thr Cys Thr
                290                 295                300

Val Thr His Thr Asp Leu Pro Ser Pro Leu Asp Gln Thr Ile Ser Arg
305                     310                 315                320

Pro Lys Gly Val Ala Leu His Arg Pro Asp Val Tyr Leu Leu Pro Pro
                325                 330                335

Ala Arg Glu Gln Leu Asn Leu Arg Glu Ser Ala Thr Ile Thr Cys Leu
                340                 345                350

Val Thr Gly Phe Ser Pro Ala Asp Val Phe Val Gln Trp Met Gln Arg
                355                 360                365

Gly Gln Pro Leu Ser Pro Glu Lys Tyr Val Thr Ser Ala Pro Met Pro
                370                 375                380

Glu Pro Gln Ala Pro Gly Arg Tyr Phe Ala His Ser Ile Leu Thr Val
385                     390                 395                400

Ser Glu Glu Glu Trp Asn Thr Gly Glu Thr Tyr Thr Cys Val Val Ala
                405                 410                415

His Glu Ala Leu Pro Asn Arg Val Thr Glu Arg Thr Val Asp Lys Ser
                420                 425                430
```

Thr Gly Lys Pro Thr Leu Tyr Asn Val Ser Leu Val Met Ser Asp Thr
        435                 440                 445

Ala Gly Thr Cys Tyr
    450

<210> SEQ ID NO 25
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Ser Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Gln Gln Thr Ile Ser Arg
305                 310                 315                 320

Pro Lys Gly Val Ala Leu His Arg Pro Asp Val Tyr Leu Leu Pro Pro

```
                    325                 330                 335
Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
        370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
                420                 425                 430

Thr Gly Lys Pro Thr Leu Tyr Asn Val Ser Leu Val Met Ser Asp Thr
            435                 440                 445

Ala Gly Thr Cys Tyr
        450

<210> SEQ ID NO 26
<211> LENGTH: 8
<212> TYPE: PRT
<213> ORGANISM: Homo sapiens

<400> SEQUENCE: 26

Asp Leu Pro Ser Pro Leu Lys Gln
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ala Pro Ser Pro Leu Lys Gln
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Leu Ala Ser Pro Leu Lys Gln
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Leu Pro Ser Ser Leu Lys Gln
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Leu Pro Ser Pro Leu Ala Gln
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Pro Ser Pro Leu Lys Gln
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Leu Pro Ser Pro Leu Asp Gln
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Leu Pro Ser Pro Leu Gln Gln
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ala Pro Ser Pro Leu Ala Gln
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Asp Ser Pro Ser Pro Leu Ser Gln
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Ala Ala Ser Pro Leu Lys Gln
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Ala Pro Ser Ser Leu Lys Gln
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Leu Ala Ser Pro Leu Ala Gln
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Leu Pro Ser Ser Leu Ala Gln
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Leu Ala Ser Ser Leu Lys Gln
1               5
```

MODIFIED HUMAN IGM CONSTANT REGIONS FOR MODULATION OF COMPLEMENT-DEPENDENT CYTOLYSIS EFFECTOR FUNCTION

CROSS-REFERENCE TO RELATED APPLICATIONS

This application is a US National Stage Entry of PCT Application No. PCT/US2018/026474, filed Apr. 6, 2018, which claims the benefit of U.S. Provisional Patent Application Ser. No. 62/483,087, filed Apr. 7, 2017, which are each incorporated herein by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Aug. 10, 2021, is named 010US1-Updated-Sequence-Listing and is 89958 bytes in size.

BACKGROUND

Complement dependent cytotoxicity is an effector function used by antibodies to engage components of the innate immune system to destroy invading microbes. Therapeutic antibodies can use the complement system to engage the complement system to attack cells targeted by the antibody, for example, tumor cells. The complement cascade is triggered by binding of the first component C1q to the Fc region of IgG's or to the Fc Mu region of IgM's. Hexamerization of antibodies results in formation of the hexameric C1q complex that further triggers downstream complement components and ends in formation of the membrane attack complex (MAC), which causes cell death by perforation of the cell membrane and resulting osmotic shock. Antibodies of the IgM isotype are multimeric (pentamers and hexamers) and are particularly well suited to binding and multimerization of C1q. Indeed, IgM antibodies can fix complement between 30 to 100 times better than corresponding IgG antibodies.

For those indications where an IgM antibody is used to multimerize a cell surface receptor to affect downstream signaling, however, it is not always desirable to retain this powerful complement fixation ability. For example, IgM antibodies could be used to activate T-cells by engaging TNF receptor superfamily members like CD40, OX40 or GITR. In each case, multimerization driven downstream signaling can be used to cause powerful agonist activity and proliferation of T-cells. However, if the complement fixation activity of IgM antibody is left intact, it could potentially counteract the agonist activity of IgM antibody on these targets. For this reason, there is a need in the art to identify mutations of the IgM heavy chain constant region that could reduce or eliminate complement fixation and resultant complement dependent cytotoxicity (CDC activity).

Mutations that enhance or reduce CDC activity in mouse IgM have been identified. See, e.g., Arya, S., et al., *J. Immunol.* 152: 1206-1212 (1994), Wright, J, F., et al., *J. Biol. Chem.* 263:11221-11226 (1988), and Wright, J. F., et al., *J. Biol. Chem.* 265:10506-10513 (1989). There remains a need in the art to identify and characterize modified human IgM antibodies with modified CDC activity.

SUMMARY

This disclosure provides a modified human IgM constant region that includes one or more amino acid substitutions relative to a wild-type human IgM constant region, where at least one amino acid substitution is at a position in the Cµ3 domain ranging from T302 of SEQ ID NO: 1 to K322 of SEQ ID NO: 1, and where a modified IgM antibody that includes the modified IgM constant region and a heavy chain variable region specific for a target antigen exhibits reduced complement-dependent cytotoxicity (CDC) of cells expressing the target antigen relative to a corresponding wild-type human IgM antibody.

In certain aspects, the modified human IgM constant region includes at least one amino acid substitution is at amino acid T302, C303, T304, V305, T306, H307, T308, D309, L310, P311, S312, P313, L314, K315, Q316, T317, I318, S319, R320, P321, and/or K322 of SEQ ID NO: 1. For example, the modified human IgM constant region can include at least one amino acid substitution is at position L310 of SEQ ID NO: 1, position P311 of SEQ ID NO: 1, position P313 of SEQ ID NO: 1, position K315 of SEQ ID NO: 1, or any combination thereof.

In certain aspects at least one amino acid substitution can be at position L310 of SEQ ID NO: 1, e.g., L310 of SEQ ID NO: 1 can be substituted with alanine (L310A), serine (L310S), aspartic acid (L310D) or glycine (L310G). In certain aspects L310 of SEQ ID NO: 1 can be substituted with alanine (L310A), for example, the modified IgM constant region can include SEQ ID NO: 15. In certain aspects L310 of SEQ ID NO: 1 can be substituted with aspartic acid (L310D), for example, the modified IgM constant region can include SEQ ID NO: 23.

In certain aspects at least one amino acid substitution can be at position P311 of SEQ ID NO: 1, e.g., P311 of SEQ ID NO: 1 can be substituted with alanine (P311A), serine (P311S), or glycine (P311G). In certain aspects P311 of SEQ ID NO: 1 can be substituted with alanine (P311A), for example, the modified IgM constant region can include SEQ ID NO: 2.

In certain aspects at least one amino acid substitution can be at position P313 of SEQ ID NO: 1, e.g., P313 of SEQ ID NO: 1 can be substituted with alanine (P313A), serine (P313S), or glycine (P313G). In certain aspects P313 of SEQ ID NO: 1 can be substituted with serine (P313S), for example the modified IgM constant region can include SEQ ID NO: 3.

In certain aspects at least one amino acid substitution can be at position K315 of SEQ ID NO: 1, e.g., K315 of SEQ ID NO: 1 can be substituted with alanine (K315A), serine (K315S), aspartic acid (K315D), glutamine (K315Q), or glycine (P313G). In certain aspects K315 of SEQ ID NO: 1 can be substituted with alanine (K315A), for example the modified IgM constant region can include SEQ ID NO: 16. In certain aspects K315 of SEQ ID NO: 1 can be substituted with aspartic acid (K315D), for example the modified IgM constant region can include SEQ ID NO: 24. In certain aspects K315 of SEQ ID NO: 1 can be substituted with glutamine (K315Q), for example the modified IgM constant region can include SEQ ID NO: 25.

In certain aspects the modified human IgM constant region as provided herein can include two or more amino acid substitutions. For example, the modified human IgM constant region as provided herein can include amino acid substitutions at two or more of positions L310, P311, P313, or K315 of SEQ ID NO: 1.

In certain aspects, the modified human IgM constant region as provided herein can include amino acid substitutions at positions P311 and P313 of SEQ ID NO: 1. For example, P311 of SEQ ID NO: 1 can be substituted with alanine (P311A), serine (P311S), or glycine (P311G), and P313 of SEQ ID NO: 1 can be substituted with alanine (P313A), serine (P313S), or glycine (P313G). In certain aspects, P311 of SEQ ID NO: 1 can be substituted with alanine (P311A) and P313 of SEQ ID NO: 1 can be substituted with serine (P313S), for example the modified IgM constant region can include SEQ ID NO: 4.

In certain aspects, the modified human IgM constant region as provided herein can include amino acid substitutions at positions L310 and K315 of SEQ ID NO: 1. For example, L310 can be substituted with alanine (L310A) or serine (L310S) and K315 can be substituted with alanine (K315A) or serine (K315S), for example the modified IgM constant region can include SEQ ID NO: 17 or SEQ ID NO: 18.

In certain aspects, the modified human IgM constant region as provided herein can include amino acid substitutions at positions L310 and P311 of SEQ ID NO: 1. For example, L310 can be substituted with alanine (L310A) and P311 can be substituted with alanine (P311A), for example the modified IgM constant region can include SEQ ID NO: 19.

In certain aspects, the modified human IgM constant region as provided herein can include amino acid substitutions at positions L310 and P313 of SEQ ID NO: 1. For example, L310 can be substituted with alanine (L310A) and P313 can be substituted with serine (P313S), for example the modified IgM constant region can include SEQ ID NO: 20.

In certain aspects, the modified human IgM constant region as provided herein can include amino acid substitutions at positions P311 and K315 of SEQ ID NO: 1. For example, P311 can be substituted with alanine (P311A) and K315 can be substituted with alanine (K315A), for example the modified IgM constant region can include SEQ ID NO: 21.

In certain aspects, the modified human IgM constant region as provided herein can include amino acid substitutions at positions P313 and K315 of SEQ ID NO: 1. For example, P313 can be substituted with serine (P313S) and K315 can be substituted with alanine (K315A), for example the modified IgM constant region can include SEQ ID NO: 22.

In certain aspects, the maximum CDC activity achieved in a dose response assay by a target-specific IgM antibody that includes the modified human IgM constant region as provided herein is reduced by at least 5%, 10%, 20%, 30%, 40%, 50%, 60%, 70%, 80%, 90%, 95%, or 100% relative to a corresponding wild-type IgM antibody identical except for the modified human IgM constant region.

In certain aspects, the antibody concentration effecting 50% CDC activity ($EC_{50}$) of a target-specific IgM antibody that includes the modified human IgM constant region as provided herein is increased by at least 2-fold, at least 5-fold, at least 10-fold, at least 20-fold, and least 30-fold, at least 40-fold, at least 50-fold, at least 60-fold, at least 70-fold, at least 80-fold, at least 90-fold, or at least 100-fold relative to a corresponding wild-type IgM antibody identical except for the modified human IgM constant region.

The disclosure further provides a modified human IgM antibody that includes the modified human IgM constant region as provided herein and further includes a heavy chain variable region (VH) situated amino terminal to the modified human IgM constant region, where the modified human IgM antibody specifically binds to a target antigen and exhibits reduced complement-dependent cytotoxicity (CDC) of cells expressing the target antigen relative to a corresponding wild-type human IgM antibody. In certain aspects, the modified human IgM antibody can be a pentameric or a hexameric antibody that includes five or six bivalent IgM binding units, respectively, where each binding unit includes two IgM heavy chains each including a VH situated amino terminal to the modified human IgM constant region, and two immunoglobulin light chains each including a light chain variable domain (VL) situated amino terminal to a human immunoglobulin light chain constant region. In certain aspects, the modified human IgM antibody as provided herein can be pentameric, further including a J-chain, or functional fragment thereof, or a functional variant thereof. In certain aspects the J-chain can include amino acids 23 to 158 of SEQ ID NO: 7 or functional fragment thereof, or a functional variant thereof. In certain aspects the J-chain or fragment or variant thereof can be a modified J-chain that further includes a heterologous polypeptide, where the heterologous polypeptide is directly or indirectly fused to the J-chain or fragment or variant thereof. In certain aspects the heterologous polypeptide can be fused to the J-chain or fragment thereof via a peptide linker, e.g., a peptide linker includes at least 5 amino acids, but no more than 25 amino acids. In certain aspects the peptide linker can comprise, consist essentially of, or consist of GGGGSGGGGSGGGGS (SEQ ID NO: 12). In certain aspects, the heterologous polypeptide can be fused to the N-terminus of the J-chain or fragment or variant thereof, the C-terminus of the J-chain or fragment or variant thereof, or to both the N-terminus and C-terminus of the J-chain or fragment or variant thereof. In certain aspects, the heterologous polypeptide can include a binding domain, e.g., an antibody or antigen-binding fragment thereof, e.g., an Fab fragment, an Fab' fragment, an F(ab')2 fragment, an Fd fragment, an Fv fragment, a single-chain Fv (scFv) fragment, a disulfide-linked Fv (sdFv) fragment, or any combination thereof. In certain aspects the modified J-chain can include a scFv fragment. In certain aspects, the heterologous polypeptide can specifically bind to CD3ε. In certain aspects, the modified J-chain can include the amino acid sequence SEQ ID NO: 9 (V15J) or SEQ ID NO: 11 (J15V). In certain aspects the modified J-chain can further include a signal peptide, e.g., the modified J-chain can include the amino acid sequence SEQ ID NO: 8 (V15J) or SEQ ID NO: 10 (J15V). In certain aspects the modified human IgM antibody as provided herein can direct T-cell-mediated killing of a cell expressing the target antigen at an activity level equivalent to that of a corresponding IgM antibody that is identical to the modified IgM antibody except for the modified IgM constant region. In certain aspects, the cell expressing the target antigen is a eukaryotic cell.

This disclosure further provides a polynucleotide that includes a nucleic acid sequence that encodes the modified human IgM constant region as provided herein, or a heavy chain polypeptide subunit of the modified human IgM antibody as provided herein. Also provided is a composition that includes the provided polynucleotide. In certain aspects the composition further includes a nucleic acid sequence that encodes a light chain polypeptide subunit. In certain aspects, the light chain polypeptide subunit includes a human antibody light chain constant region or fragment thereof fused to the C-terminal end of a VL. In certain aspects the nucleic acid sequence encoding the heavy chain polypeptide subunit and the nucleic acid sequence encoding the light chain polypeptide subunit can be on separate vectors. In certain aspects, the nucleic acid sequence encoding the heavy chain polypeptide subunit and the nucleic acid sequence encoding the light chain polypeptide subunit can be on a single vector. In certain aspects, the composition further includes a nucleic acid sequence that encodes a J-chain, or functional fragment thereof, or a functional variant thereof. In certain aspects, the J-chain or fragment or variant thereof is a modified J-chain that further includes a heterologous polypeptide, where the heterologous polypeptide is directly or indirectly fused to the J-chain or fragment thereof. In certain aspects, the nucleic acid sequence encoding the heavy chain polypeptide subunit, the nucleic acid sequence encoding the light chain polypeptide subunit, and the nucleic acid sequence encoding the J-chain can be on a single vector. In certain aspects, the nucleic acid sequence encoding the heavy chain polypeptide subunit, the nucleic acid sequence encoding the light chain polypeptide subunit, and the nucleic acid sequence encoding the J-chain can be each on separate vectors. All such vector or vectors are further provided by this disclosure. The disclosure further provides a host cell that includes the provided polynucleotides, compositions, vector, or vectors. In certain aspects, the host cell can express the modified human IgM constant region as provided herein, or the modified human IgM antibody as provided herein, or any functional fragment thereof. The disclosure further provides a method of producing the modified human IgM constant region as provided herein or the modified human IgM antibody as provided herein, where the method includes culturing the provided host cell, and recovering the constant region or antibody.

BRIEF DESCRIPTION OF THE DRAWINGS/FIGURES

FIG. 1 shows an SDS PAGE gel run under non-reducing conditions to show assembly of pentamers and hexamers. Gel patterns are depicted for the controls, IgM (pure), IgM+J (pure), and supernatant preparations (all without J chain) of IgM, and the IgM mutants, S283N, P313S, P311A, and D294G.

FIG. 2 shows percent complement dependent cytolysis (CDC) activity for 1) control anti-CD20 antibodies tested in the absence of complement (1.5.3 IgG and 1.5.3 IgM×V15J); 2) for control IgM (1.5.3 IgM, without J-chain) tested in the presence of complement; and 3) for corresponding 1.5.3 IgM mutants P311A, P313S, D294G, and S283N, all without J-chain, tested in the presence of complement.

Figure 8:
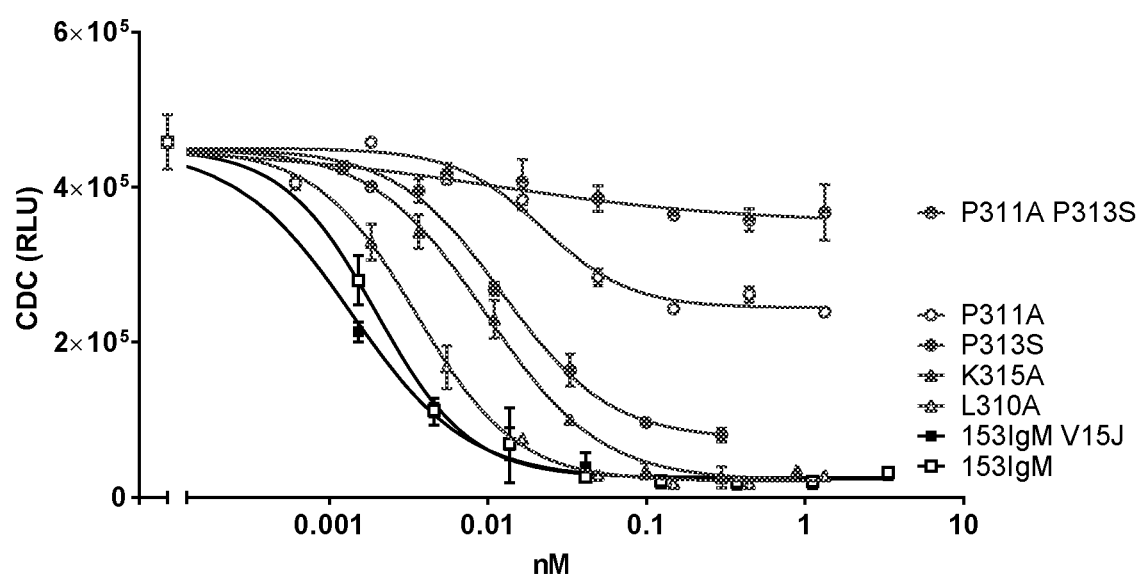

FIG. 8 shows CDC activity for 1.5.3 IgM without J-chain, 1.5.3 IgM×V15J, the corresponding 1.5.3×V15J IgM mutants, P311A, P313S, L310A, K315A, and the double mutant P311A/P313S. The double mutant shows complete elimination of CDC activity. Figure discloses SEQ ID NO: 41.

Figures 9A, 9B:
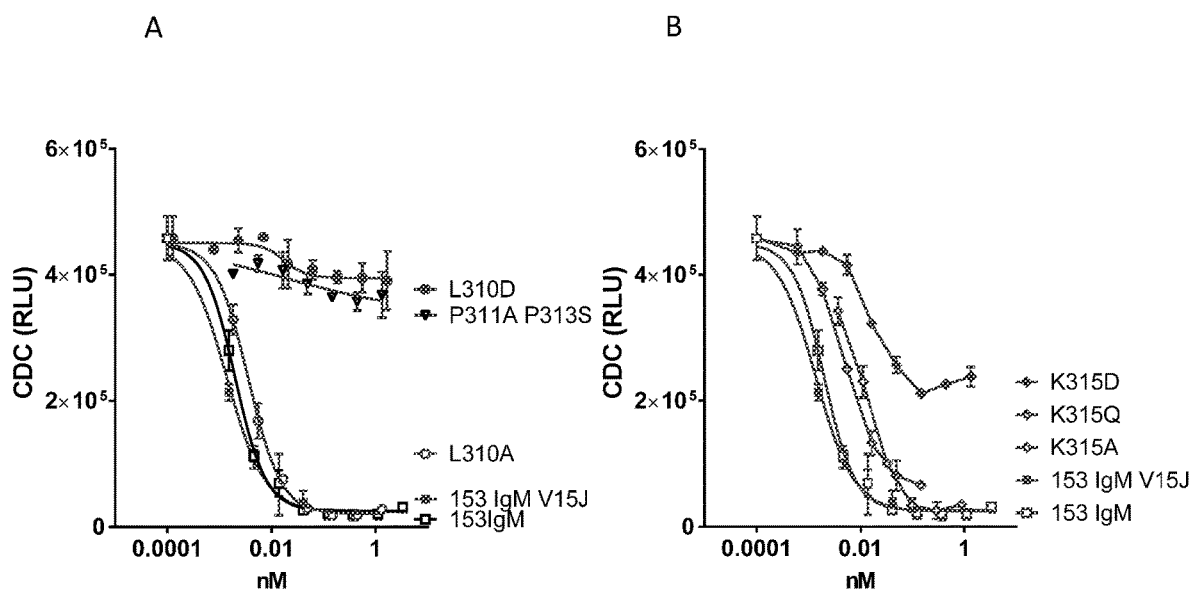

FIG. 9A shows CDC activity for 1.5.3 IgM without J-chain, 1.5.3 IgM×V15J, the 1.5.3×V15J IgM mutants L310D and L310A, and the double mutant P311A/P313S.

FIG. 9B shows CDC activity for 1.5.3 IgM without J-chain, 1.5.3 IgM×V15J, and the 1.5.3×V15J IgM mutants K315D, K315Q, and K315A.

DETAILED DESCRIPTION

Definitions

The term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt many different conformations, are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "a non-naturally occurring polypeptide" or any grammatical variants thereof, is a conditional definition that explicitly excludes, but only excludes, those forms of the polypeptide that are, or could be, determined or interpreted by a judge or an administrative or judicial body, to be "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, the term "a non-naturally occurring polynucleotide" or any grammatical variants thereof, is a conditional definition that explicitly excludes, but only excludes, those forms of the nucleic acid or polynucleotide that are, or could be, determined or interpreted by a judge, or an administrative or judicial body, to be "naturally-occurring."

As used herein, a "coding region" is a portion of nucleic acid which consists of codons translated into amino acids.

Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse ß-glucuronidase.

As used herein, the term "CD20" refers to a membrane protein expressed on the surface of B lymphocytes. The CD20 protein is referred to in the literature by other names, e.g., B-lymphocyte antigen CD20, B-lymphocyte cell-surface antigen B1, Bp35, CVID5, LEU-16, Membrane-spanning 4-domains subfamily A member 1, or MS4A2. Certain multivalent anti-CD20 binding molecules, e.g., IgM antibodies or fragments thereof as disclosed herein are further described in PCT Publication No. WO/2016/141303, which is incorporated herein by reference in its entirety.

Disclosed herein are certain binding molecules, or antigen-binding fragments, variants, or derivatives thereof. Unless specifically referring to full-sized antibodies, the term "binding molecule" includes full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a target or molecular determinant, e.g., an epitope or an antigenic determinant. As described further herein, a binding molecule can comprise one or more "antigen binding domains" described herein. A non-limiting example of a binding molecule is an antibody or fragment thereof that retains antigen-specific binding.

As used herein, the terms "binding domain" or "antigen binding domain" refer to a region of a binding molecule that is sufficient to specifically bind to an epitope. For example, an "Fv," e.g., a variable heavy chain and variable light chain of an antibody, either as two separate polypeptide subunits or as a single chain, is considered to be a "binding domain." Other antigen binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable domain of a heavy chain (for camelid species) or at least the variable domains of a heavy chain and a light chain. Basic immunoglobulin structures in vertebrate systems are relatively well understood. (See, e.g., Harlow et al., Antibodies: A Laboratory Manual, Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and can include a J-chain and/or a secretory component, or an IgM antibody that includes ten or twelve complete heavy chains and ten or twelve complete light chains and can include a J-chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$ or $\alpha1$-$\alpha2$)). It is the nature of this chain that determines the "isotype" of the antibody as IgG, IgM, IgA IgG, or IgE, respectively. The immunoglobulin subclasses (subtypes) e.g., $IgG_1$, $IgG_2$, $IgG_3$, $IgG_4$, $IgA_1$, $IgA_2$, are well characterized and are known to confer functional specialization. Modified versions of each of these immunoglobulins are readily discernible to the skilled artisan in view of the instant disclosure and, accordingly, are within the scope of this disclosure. In certain embodiments, this disclosure provides modified human IgM antibodies.

Light chains are classified as either kappa or lambda (x, X). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are expressed, e.g., by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure, or a "binding unit."

The term "binding unit" is used herein to refer to the portion of a binding molecule, e.g., an antibody or antigen-binding fragment thereof, which corresponds to a standard immunoglobulin structure, e.g., two heavy chains or fragments thereof and two light chains or fragments thereof, or two heavy chains or fragments thereof derived, e.g., from a camelid or condricthoid antibody. In certain aspects, e.g., where the binding molecule is a bivalent IgG antibody or antigen-binding fragment thereof, the terms "binding molecule" and "binding unit" are equivalent. In other aspects, e.g., where the binding molecule is an IgM pentamer or an IgM hexamer, the binding molecule comprises two or more "binding units," five or six in the case of an IgM pentamer or hexamer, respectively. A binding unit need not include full-length antibody heavy and light chains, but will typically be bivalent, i.e., will include two "antigen binding domains," as defined below. Certain IgM-derived binding molecules provided in this disclosure are pentameric or hexameric and include five or six bivalent binding units that include IgM constant regions, e.g., modified human IgM constant regions, or fragments thereof. As used herein, a binding molecule comprising two or more binding units, e.g., five or six binding units, can be referred to as "multimeric."

The terms "J-chain," "native sequence J-chain" or "native J-chain" as used herein refers to J-chain of native sequence IgM or IgA antibodies of any animal species, including mature human J-chain, the amino acid sequence of which is presented as SEQ ID NO: 7.

The term "modified J-chain" is used herein to refer to variants of native sequence J-chain polypeptides comprising a heterologous moiety, e.g., a heterologous polypeptide, e.g., an extraneous binding domain introduced into the native sequence. The introduction can be achieved by any means, including direct or indirect fusion of the heterologous polypeptide or other moiety or by attachment through a peptide or chemical linker. The term "modified human J-chain" encompasses, without limitation, a native sequence human J-chain of the amino acid sequence of SEQ ID NO: 7 or functional fragment thereof modified by the introduction of a heterologous moiety, e.g., a heterologous polypeptide, e.g., an extraneous binding domain. In certain aspects the heterologous moiety does not interfere with efficient polymerization of IgM into a pentamer and binding of such polymers to a target. Exemplary modified J-chains can be found, e.g., in PCT Publication No. WO 2015/153912, in PCT Publication No. WO/2017/059387, and in PCT Publication No. WO/2017/059380, each of which is incorporated herein by reference in its entirety.

The terms "valency," "bivalent," "multivalent" and grammatical equivalents, refer to the number of antigen binding domains in given binding molecule or binding unit. As such, the terms "bivalent", "tetravalent", and "hexavalent" in reference to a given binding molecule, e.g., an IgM antibody or fragment thereof, denote the presence of two antigen binding domains, four antigen binding domains, and six antigen binding domains, respectively. In a typical IgM-derived binding molecule where each binding unit is bivalent, the binding molecule itself can have 10 or 12 valencies. A bivalent or multivalent binding molecule can be monospecific, i.e., all of the antigen binding domains are the same, or can be bispecific or multispecific, e.g., where two or more antigen binding domains are different, e.g., bind to different epitopes on the same antigen, or bind to entirely different antigens.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three-dimensional structural characteristics, and or specific charge characteristics. An epitope is a region of a target that is bound by an antibody.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant regions of the light chain (CL) and the heavy chain (e.g., CH1, CH2, CH3, or CH4) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains are at the carboxy-terminus of the heavy and light chain, respectively.

A "full length IgM antibody heavy chain" is a polypeptide that includes, in N-terminal to C-terminal direction, an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4) that can include a tailpiece.

As indicated above, a variable region (i.e., the "antigen binding domain") allows a binding molecule to selectively recognize and specifically bind epitopes on antigens. That is, the VL domain and VH domain (or just a VH domain for camelid or condricthoid antibodies (designated as VHH)), or subset of the complementarity determining regions (CDRs), of a binding molecule, e.g., an antibody, can combine to form the antigen binding domain. More specifically, an antigen binding domain can be defined by three CDRs on each of the VH and VL chains (or 3 CDRs on a VHH). Certain antibodies form larger structures. For example, IgM can form a dimeric, pentameric, or hexameric molecule that includes two, five, or six H2L2 binding units and optionally a J-chain covalently connected via disulfide bonds.

The six "complementarity determining regions" or "CDRs" present in an antibody antigen binding domain are short, non-contiguous sequences of amino acids that are specifically positioned to form the antigen binding domain as the antibody assumes its three-dimensional configuration in an aqueous environment. The remainder of the amino acids in the antigen binding domain, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

| CDR Definitions* | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Immunoglobulin variable domains can also be analyzed, e.g., using the IMGT information system (www://imgt.cines.fr/) (IMGT®/V-Quest) to identify variable region segments, including CDRs. See, e.g., Brochet, X. et al., *Nucl. Acids Res.* 36:W503-508 (2008).

Kabat et al. also defined a numbering system for variable and constant region sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for amino acid sequences in this disclosure. Another numbering scheme is the Eu numbering system for IgG (Edelman, G M, et al., *Proc. Natl. Acad. Sci. USA* 63:78-85 (1969)), which has been adapted for other immunoglobulins including IgM (see, e.g., Arya, S., et al., *J. Immunol.* 152: 1206-1212 (1994)).

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5\times10^{-2}$ sec$^{-1}$, $10^{-2}$ sec$^{-1}$, $5\times10^{-3}$ sec$^{-1}$, $10^{-3}$ sec$^{-1}$, $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^{3}$ M$^{-1}$ sec$^{-1}$, $5\times10^{3}$ M$^{-1}$ sec$^{-1}$, $10^{4}$ M$^{-1}$ sec$^{-1}$, $5\times10^{4}$ M$^{-1}$ sec$^{-1}$, $10^{5}$ M$^{-1}$ sec$^{-1}$, $5\times10^{5}$ M$^{-1}$ sec$^{-1}$, $10^{6}$ M$^{-1}$ sec$^{-1}$, or $5\times10^{6}$ M$^{-1}$ sec$^{-1}$ or $10^{7}$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more antigen binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross-reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Antibody fragments including single-chain antibodies or other antigen binding domains can exist alone or in combination with one or more of the following: hinge region, CH1, CH2, CH3, or CH4 domains, J-chain, or secretory component. Also included are antigen-binding fragments that can include any combination of variable region(s) with one or more of a hinge region, CH1, CH2, CH3, or CH4 domains, a J-chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, without limitation, in addition to a VH domain: a CH1 domain; a CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J-chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

As used herein, the term "light chain subunit" includes amino acid sequences derived from an immunoglobulin light chain. The light chain subunit includes at least a VL, and can further include a CL (e.g., Cκ or Cλ) domain.

Binding molecules, e.g., antibodies or antigen-binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As used herein the term "disulfide bond" includes the covalent bond formed between two sulfur atoms. The amino acid cysteine comprises a thiol group that can form a disulfide bond or bridge with a second thiol group.

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The term "multispecific antibody, e.g., "bispecific antibody" refers to an antibody that has antigen binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, Future Oncol. 6:1387-94 (2010); Mabry and Snavely, IDrugs. 13:543-9 (2010)). A bispecific antibody can also be a diabody.

As used herein, the term "engineered antibody" refers to an antibody in which the variable domain and/or constant region in either the heavy and light chain or both is altered by at least partial replacement of one or more amino acids in the CDR, framework, and/or constant regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects, not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly, a portion of a polypeptide that is "carboxy-terminal" or "C-terminal" to another portion of a polypeptide is that portion that comes later in the sequential polypeptide chain. For example, in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into RNA, e.g., messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a binding molecule such as an antibody, comprising one or more antigen binding domains. Such binding molecules, e.g., antibodies, can be used, e.g., for diagnostic procedures and/or for treatment or prevention of a disease.

IgM Binding Molecules

IgM is the first immunoglobulin produced by B cells in response to stimulation by antigen and is present at around 1.5 mg/ml in serum with a half-life of 5 days. IgM is typically a pentameric or hexameric molecule. An IgM binding unit typically includes two light chains and two heavy chains. While IgG contains three heavy chain constant domains (CH1, CH2 and CH3), the heavy (µ) chain of IgM additionally contains a fourth constant domain (CH4), that includes a C-terminal "tailpiece." The human IgM constant region typically comprises the amino acid sequence SEQ ID NO: 1 (see Table 3). The human Cµ1 region ranges from about amino acid 5 to about amino acid 102 of SEQ ID NO: 1; the human Cµ2 region ranges from about amino acid 114 to about amino acid 205 of SEQ ID NO: 1, the human Cµ3 region ranges from about amino acid 224 to about amino acid 319 of SEQ ID NO: 1, the Cµ4 region ranges from about amino acid 329 to about amino acid 430 of SEQ ID NO: 1, and the tailpiece ranges from about amino acid 431 to about amino acid 453 of SEQ ID NO: 1.

Five IgM binding units can form a complex with an additional small polypeptide chain (the J-chain) to form an IgM antibody. The precursor human J-chain comprises the amino acid sequence SEQ ID NO: 7 (Table 3). The first 22 amino acids of SEQ ID NO: 7 is the secretory signal peptide and the mature human J-chain starts at amino acid 23 of SEQ ID NO: 7. Without the J-chain, IgM binding units typically assemble into a hexamer. While not wishing to be bound by theory, the assembly of IgM binding units into a hexameric or pentameric binding molecule is thought to involve the C3, Cµ4 and tailpiece domains. Accordingly, a hexameric or pentameric binding molecule provided in this disclosure typically includes IgM constant regions that include at least the Cµ3, Cµ4, and tailpiece domains.

An IgM heavy chain constant region can additionally include a Cµ2 domain or a fragment thereof, a Cµ1 domain or a fragment thereof, and/or other IgM heavy chain domains. In certain aspects, a binding molecule as provided herein can include a complete IgM heavy (µ) chain constant region (e.g., SEQ ID NO: 1), or a variant, derivative, or analog thereof.

The Complement System and Complement-Dependent Cytotoxicity

The complement system comprises more than 30 glycoproteins, from which 20 are present in plasma and 10 are cell-associated regulators or receptors. Activation of the complement cascade induces diverse immune effector functions including cell lysis, phagocytosis, chemotaxis and immune cell activation. Complement can be activated by 3 different pathways: the classical, the alternative and the mannose-binding lectin pathway which all converge on the level of C3 protein and lead to complement-dependent cytotoxicity of the target cell by the formation of the membrane-attack complex (MAC). IgM and certain subclasses of IgG antibodies in immune complexes activate the classical complement pathway. The formation of an antigen-antibody complex induces conformational changes in the Fc portion of the IgM or IgG molecule that expose a binding site for the C1 component of the complement system. C1 in serum is a macromolecular complex consisting of C1q and two molecules each of C1r and C1s. Binding of C1q to Fc-binding sites induces a conformational change in C1r and C1s. Subsequently, proteolytically activated C1r cleaves C1s resulting in C1s activation. C1s then cleaves C2 and C4 to generate C2a, C2b, C4a, and C4b. C2a and C4b together form the C3 convertase. The cleavage of the central component C3 by the C3 convertase leads to formation of C3b, some of which binds to the plasma membrane of the target cell. Membrane-bound C3b interacts with the C3 convertase, leading to the formation of the C5 convertase. Consequently, C5 is cleaved into C5a and C5b. The activation of the terminal pathway leads to the deposition of the components C5b-C9 into the opsonized target cell membrane forming the membrane-attack complex, eventually causing complement dependent cytotoxicity (CDC).

The end result of complement dependent cytolysis is the formation of a pore in the lipid bilayer membrane of a cell that destroys membrane integrity. Complement-dependent cytotoxicity assays (CDC assays) test the efficacy of antibodies to activate the complement immune pathway to initiate a membrane-attack complex and lysis of targeted cells. One method for a CDC assay is to mix target cells bound by the antibody being evaluated with an additive, e.g., serum, that contains the components of the complement system and then measure cell death. Cell death can be measured, e.g., by pre-loading the target cells with a radioactive compound, which upon death is released from the cells, and the efficacy of the antibody to mediate cell death is measured by radioactivity level. Non-radioactive CDC assays, e.g., the CELLTITER-GLO® assay available from Promega, measure the release of abundant cell components, like ATP, with fluorescent or luminescent measurements. In the event of CDC, the mixture results in cell lysis and generation of a luminescent signal proportional to the amount of ATP present. The amount of ATP is directly proportional to the number of cells present in culture.

Modified Human IgM Constant Regions with Reduced CDC Activity

This disclosure provides a modified human IgM constant region that, when expressed as part of a modified target-specific human IgM antibody directed to a target antigen expressed on a cell, exhibits reduced CDC activity of the cell in the presence of complement, relative to a corresponding wild-type human IgM antibody. By "corresponding wild-type human IgM antibody" is meant a wild-type IgM antibody that is identical to the antibody comprising the modified human IgM constant region except for the modification or modifications in the constant region affecting CDC activity. For example, the "corresponding wild-type human IgM antibody" will comprise identical VH and VL regions and any other modifications or truncations that that the modified human IgM antibody might have other than the modifications affecting CDC activity. In certain aspects, the modified human IgM constant region comprises one or more amino acid substitutions, e.g., in or close to the Cµ3 domain, e.g., in the region extending from about amino acid T302 of SEQ ID NO: 1 to about amino acid K322 of SEQ ID NO: 1, e.g., at least one, at least two, or at least three or more amino acid substitutions at position T302, C303, T304, V305, T306, H307, T308, D309, L310, P311, S312, P313, L314, K315, Q316, T317, I318, S319, R320, P321, and/or K322 of SEQ ID NO: 1 relative to a wild-type human IgM constant region. While not wishing to be bound by theory, the C1q component of complement is thought to associate with the human IgM constant region at least through certain amino acid residues present in the Cµ3 domain. Assays for measuring CDC are well known to those of ordinary skill in the art, and exemplary assays are described herein.

In certain aspects, a modified human IgM constant region as provided herein comprises a substitution relative to a wild-type human IgM constant region at position P311 of SEQ ID NO: 1. In other aspects a modified IgM constant region as provided herein comprises a substitution relative to a wild-type human IgM constant region at position P313 of SEQ ID NO: 1. In other aspects a modified IgM constant region as provided herein comprises a substitution relative to a wild-type human IgM constant region at position L310 of SEQ ID NO: 1. In other aspects a modified IgM constant region as provided herein comprises a substitution relative to a wild-type human IgM constant region at position K315 of SEQ ID NO: 1. In other aspects a modified IgM constant region as provided herein contains a combination of substitutions relative to a wild-type human IgM constant region at two or more of positions L310 of SEQ ID NO: 1, P311 of SEQ ID NO: 1, P313 of SEQ ID NO: 1, and/or K315 of SEQ ID NO: 1. A modified IgM constant region as provided herein can be substituted at amino acid position P311 of SEQ ID NO: 1 with, e.g., alanine (P311A) (SEQ ID NO: 2), serine (P311S), or glycine (P311G). A modified IgM constant region as provided herein can be substituted at amino acid position P313 of SEQ ID NO: 1 with, e.g., alanine (P313A), serine (P313S) (SEQ ID NO: 3), or glycine (P313G). A modified IgM constant region as provided herein can be substituted at amino acid position L310 of SEQ ID NO: 1 with, e.g., alanine (L310A) (SEQ ID NO: 15), serine (L310S), glycine (L310G), or aspartic acid (L310D) (SEQ ID NO: 23). A modified IgM constant region as provided herein can be substituted at amino acid position K315 of SEQ ID NO: 1 with, e.g., alanine (K315A) (SEQ ID NO: 16), serine (K315S), glycine (K315G), aspartic acid (K315D) (SEQ ID NO: 24), or glutamine (K315Q) (SEQ ID NO: 25). A modified IgM constant region as provided herein can be substituted at amino acid positions P311 and P313 of SEQ ID NO: 1 with, e.g., alanine (P311A) and serine (P313S), respectively (SEQ ID NO: 4), or any combination of alanine, serine, and/or glycine. A modified IgM constant region as provided herein can be substituted at amino acid positions L310 and K315 of SEQ ID NO: 1 with, e.g., alanine (L310A, K315A) (SEQ ID NO: 17), or serine (L310S, K315S) (SEQ ID NO: 18), or any combination of alanine, serine, aspartic acid, glutamine, and/or glycine. A modified IgM constant region as provided herein can be substituted at amino acid positions L310 and P311 of SEQ ID NO: 1 with, e.g., alanine (L310A, P311A) (SEQ ID NO: 19), or any combination of alanine, serine, aspartic acid, glutamine, and/or glycine. A modified IgM constant region as provided herein can be substituted at amino acid positions L310 and P313 of SEQ ID NO: 1 with, e.g., alanine and serine, respectively (L310A, P313S) (SEQ ID NO: 20), or any combination of alanine, serine, aspartic acid, glutamine, and/or glycine. A modified IgM constant region as provided herein can be substituted at amino acid positions P311 and K315 of SEQ ID NO: 1 with, e.g., alanine (P311A, K315A) (SEQ ID NO: 21), or any combination of alanine, serine, aspartic acid, glutamine, and/or glycine. A modified IgM constant region as provided herein can be substituted at amino acid positions P313 and K315 of SEQ ID NO: 1 with, e.g., serine and alanine, respectively (P313S, K315A) (SEQ ID NO: 22), or any combination of alanine, serine, aspartic acid, glutamine, and/or glycine.

In certain aspects, the complement-dependent cytotoxicity activity (CDC) of a target-specific IgM antibody comprising a modified human IgM constant region as provided herein comprising, e.g., an amino acid substitution at L310, P311, P313, and/or K315, e.g., L310A, L310S, L310G, L310D, P311A, P311S, P311G, P313A, P313S, P313G, K315A, K315S, K315G, K315D, and/or K315Q, or any combination thereof, can be reduced by at least 5%, 10%, 20%, 30%, 40%, 50%, 60%, 70%, 80%, 90%, 95%, or 100% relative to a corresponding wild-type IgM antibody, i.e., a wild-type target-specific IgM antibody that is identical except for the modified human IgM constant region.

In certain aspects, the antibody concentration effecting 50% CDC activity ($EC_{50}$) of a target-specific IgM antibody comprising a modified human IgM constant region as provided herein comprising, e.g., an amino acid substitution at L310, P311, P313, and/or K315, e.g., L310A, L310S, L310G, L310D, P311A, P311S, P311G, P313A, P313S, P313G, K315A, K315S, K315G, K315D, and/or K315Q, or any combination thereof, can be increased by at least 2-fold, at least 5-fold, at least 10-fold, at least 20-fold, and least 30-fold, at least 40-fold, at least 50-fold, at least 60-fold, at least 70-fold, at least 80-fold, at least 90-fold, or at least 100-fold relative to a corresponding wild-type IgM antibody, i.e., a wild-type target-specific IgM antibody that is identical except for the modified human IgM constant region.

Modified human IgM constant regions as provided herein can be constructed by standard mutagenesis methods well known to those of ordinary skill in the art or can be obtained from a variety of commercial vendors. Methods for mutagenesis and nucleotide sequence alterations are well known in the art. See, for example, Walker and Gaastra, eds. (1983) Techniques in Molecular Biology (MacMillan Publishing Company, New York); Kunkel, Proc. Natl. Acad. Sci. USA 82:488-492 (1985); Kunkel et al., Methods Enzymol. 154: 367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In certain aspects, conservative substitutions, such as exchanging one amino acid with another having similar properties are used. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

Pentameric or Hexameric Modified Human IgM Antibodies

In another aspect, this disclosure provides a modified human IgM antibody comprising a modified human IgM constant region as provided herein, and further comprising a heavy chain variable region (VH) situated amino terminal to the modified human IgM constant region that specifically binds to a target antigen (alone or in combination with light chain variable region (VL)) and exhibits decreased complement-dependent cytotoxicity (CDC) of cells expressing the target antigen and/or an increased antibody concentration effecting 50% CDC activity ($EC_{50}$) relative to a corresponding wild-type human IgM antibody, i.e., a wild-type target-specific IgM antibody that is identical except for the modified human IgM constant region. In certain aspects, the modified human IgM antibody comprises one or more amino acid substitutions, e.g., in or close to the Cμ3 domain, e.g., in the region extending from about amino acid T302 of SEQ ID NO: 1 to about amino acid K322 of SEQ ID NO: 1, e.g., at least one, at least two, or at least three or more amino acid substitutions at position T302, C303, T304, V305, T306, H307, T308, D309, L310, P311, S312, P313, L314, K315, Q316, T317, 1318, S319, R320, P321, and/or K322 of SEQ ID NO: 1 relative to a wild-type human IgM constant region. While not wishing to be bound by theory, the C1q component of complement is thought to associate with the human IgM constant region at least through certain amino acid residues present in the Cµ3 domain. Assays for measuring CDC are well known to those of ordinary skill in the art, and exemplary assays are described herein.

In certain aspects, a modified human IgM antibody as provided herein comprises a substitution relative to a wild-type human IgM antibody at position P311 of SEQ ID NO: 1. In other aspects, a modified human IgM antibody as provided herein contains a substitution relative to a wild-type human IgM antibody at position P313 of SEQ ID NO: 1. In other aspects a modified human IgM antibody as provided herein contains a substitution relative to a wild-type human IgM antibody at position L310 of SEQ ID NO: 1. In other aspects a modified human IgM antibody as provided herein contains a substitution relative to a wild-type human IgM antibody at position K315 of SEQ ID NO: 1. In other aspects a modified IgM antibody as provided herein contains a combination of substitutions relative to a wild-type human IgM antibody at two or more of positions L310 of SEQ ID NO: 1, P311 of SEQ ID NO: 1, P313 of SEQ ID NO: 1, and/or K315 of SEQ ID NO: 1. A modified IgM antibody as provided herein can be substituted at amino acid position P311 of SEQ ID NO: 1 with, e.g., alanine (P311A) (SEQ ID NO: 2), serine (P311S), or glycine (P311G). A modified IgM antibody as provided herein can be substituted at amino acid position P313 of SEQ ID NO: 1 with, e.g., alanine (P313A), serine (P313S) (SEQ ID NO: 3), or glycine (P313G). A modified IgM antibody as provided herein can be substituted at amino acid position L310 of SEQ ID NO: 1 with, e.g., alanine (L310A) (SEQ ID NO: 15), serine (L310S), glycine (L310G) or aspartic acid (L310D) (SEQ ID NO: 23). A modified IgM antibody as provided herein can be substituted at amino acid position K315 of SEQ ID NO: 1 with, e.g., alanine (K315A) (SEQ ID NO: 16), serine (K315S), glycine (K315G), aspartic acid (K315D) (SEQ ID NO: 24), or glutamine (K315Q) (SEQ ID NO: 25). A modified IgM antibody as provided herein can be substituted at amino acid positions P311 and P313 of SEQ ID NO: 1 with, e.g., alanine (P311A) and serine (P313S), respectively (SEQ ID NO: 4), or any combination of alanine, serine, and/or glycine. A modified IgM antibody as provided herein can be substituted at amino acid positions L310 and K315 of SEQ ID NO: 1 with, e.g., alanine (L310A, K315A) (SEQ ID NO: 17), or serine (L310S, K315S) (SEQ ID NO: 18), or any combination of alanine, serine, aspartic acid, glutamine, and/or glycine. A modified IgM antibody as provided herein can be substituted at amino acid positions L310 and P311 of SEQ ID NO: 1 with, e.g., alanine (L310A, P311A) (SEQ ID NO: 19), or any combination of alanine, serine, aspartic acid, glutamine, and/or glycine. A modified IgM antibody as provided herein can be substituted at amino acid positions L310 and P313 of SEQ ID NO: 1 with, e.g., alanine and serine, respectively (L310A, P313S) (SEQ ID NO: 20), or any combination of alanine, serine, aspartic acid, glutamine, and/or glycine. A modified IgM antibody as provided herein can be substituted at amino acid positions P311 and K315 of SEQ ID NO: 1 with, e.g., alanine (P311A, K315A) (SEQ ID NO: 21), or any combination of alanine, serine, aspartic acid, glutamine, and/or glycine. A modified IgM antibody as provided herein can be substituted at amino acid positions P313 and K315 of SEQ ID NO: 1 with, e.g., serine and alanine, respectively (P313S, K315A) (SEQ ID NO: 22), or any combination of alanine, serine, aspartic acid, glutamine, and/or glycine.

In certain aspects, the complement-dependent cytotoxicity activity (CDC) of the modified IgM antibody as provided herein comprising, e.g., an amino acid substitution at L310, P311, P313, and/or K315, e.g., L310A, L310S, L310G, L310D, P311A, P311S, P311G, P313A, P313S, P313G, K315A, K315S, K315G, K315D, and/or K315Q, or any combination thereof, can be reduced by at least 5%, 10%, 20%, 30%, 40%, 50%, 60%, 70%, 80%, 90%, 95%, or 100% relative to a corresponding wild-type IgM antibody, i.e., a wild-type target-specific IgM antibody that is identical except for the modified human IgM constant region.

In certain aspects, antibody concentration effecting 50% CDC activity ($EC_{50}$) of the IgM antibody as provided herein, comprising, e.g., an amino acid substitution at L310, P311, P313, and/or K315, e.g., L310A, L310S, L310G, L310D, P311A, P311S, P311G, P313A, P313S, P313G, K315A, K315S, K315G, K315D, and/or K315Q, or any combination thereof, can be increased by at least 2-fold, at least 5-fold, at least 10-fold, at least 20-fold, and least 30-fold, at least 40-fold, at least 50-fold, at least 60-fold, at least 70-fold, at least 80-fold, at least 90-fold, or at least 100-fold relative to a corresponding wild-type IgM antibody, i.e., a wild-type target-specific IgM antibody that is identical except for the modified human IgM constant region.

A modified human IgM antibody as provided herein can be hexameric or pentameric, comprising five or six IgM "binding units" as defined herein, one or more of which can specifically bind to a target antigen of interest. The disclosure encompasses a modified human IgM antibody that specifically binds to any target antigen. In certain aspects the target antigen is capable of expression on the surface of a cell, e.g., a eukaryotic cell. Target antigens can include, without limitation, tumor antigens, other oncologic targets, immuno-oncologic targets such as immune checkpoint inhibitors, infectious disease antigens, such as viral antigens expressed on the surface of infected cells, target antigens involved in blood-brain-barrier transport, target antigens involved in neurodegenerative diseases and neuroinflammatory diseases, and any combination thereof. Non-limiting examples of target antigens, as well as non-limiting examples of antibody binding domains that bind to such target antigens can be found, e.g., in PCT Publication Nos. WO 2016/141303, WO 2016/168758, WO 2016/154593, WO 2016/118641, WO 2015/153912, WO 2015/053887, WO 2013/120012, WO/2017/059387, WO/2017/059380, WO/2018/017888, WO/2018/017889, WO/2018/017761, and WO/2018/017763, the disclosures of which are incorporated herein by reference in their entireties.

In certain aspects, the disclosure provides a pentameric or hexameric modified human IgM antibody comprising five or six bivalent binding units, respectively, where each binding unit includes two modified human IgM heavy chain constant regions or fragments thereof as provided herein.

Where the modified human IgM antibody provided herein is pentameric, the antibody can further comprise a J-chain, or functional fragment thereof, or variant thereof. In certain aspects, the J-chain is a modified J-chain comprising a heterologous moiety or one or more heterologous moieties, e.g., a heterologous polypeptide sequence, e.g., an extraneous binding domain introduced into the native sequence. In certain aspects the extraneous binding domain specifically binds to CD3, e.g., CD3ε. In certain aspects the modified J-chain comprises V15J (SEQ ID NO: 9) or J15V (SEQ ID NO: 11).

An IgM heavy chain constant region can include one or more of a Cμ1 domain, a Cμ2 domain, a Cμ3 domain (as provided herein, the Cμ3 can comprise one or more amino acid substitutions), and/or a Cμ4 domain, provided that the constant region can serve a desired function in the modified human IgM antibody, e.g., associate with second IgM constant region to form an binding unit, or associate with other binding units to form a hexamer or a pentamer. In certain aspects the two modified human IgM heavy chain constant regions or fragments thereof within an individual binding unit each comprise a modified Cμ3 domain (e.g., with substitutions at one or more of L310 of SEQ ID NO: 1, P311 of SEQ ID NO: 1, P313 of SEQ ID NO: 1, K315 of SEQ ID NO: 1, and/or a combination thereof) or fragment thereof, a Cμ4 domain or fragment thereof, a tailpiece (TP) or fragment thereof, or any combination of a modified Cμ3 domain a Cμ4 domain, and a TP or fragment thereof. In certain aspects the two modified human IgM heavy chain constant regions or fragments thereof within an individual binding unit each further comprise a Cμ2 domain or fragment thereof, a Cμ1 domain or fragment thereof, or a Cμ1 domain or fragment thereof and a Cμ2 domain or fragment thereof.

In certain aspects each of the two modified human IgM heavy chain constant regions in a given binding unit is associated with an antigen binding domain, for example a heavy chain variable region (VH) or an Fv portion of an antibody, e.g., a VH and a VL of an antibody.

Modified J-Chains

In certain aspects a modified human IgM antibody as provided herein can be bispecific, incorporating a modified J-chain. As provided herein and in PCT Publication Nos. WO 2015/153912 WO/2017/059387, and WO/2017/059380, a modified J-chain can comprise a heterologous moiety, e.g., a heterologous polypeptide, e.g., an extraneous binding domain, which can include, for example, a polypeptide binding domain capable of specifically binding to a target. The binding domain can be, for example, an antibody or antigen-binding fragment thereof, an antibody-drug conjugate or antigen-binding fragment thereof, or an antibody-like molecule. A polypeptide binding domain can be introduced into a J-chain by appropriately selecting the location and type of addition (e.g. direct or indirect fusion, chemical tethering, etc.).

In certain aspects, the binding domain can be an antibody or an antigen-binding fragment of an antibody, including monospecific, bispecific, and multi-specific antibodies and antibody fragments. The antibody fragment can be, without limitation, a Fab fragment, a Fab' fragment, a F(ab')2 fragment, an scFv, (scFv)$_2$ fragment, single-chain antibody molecules, minibodies, or multispecific antibodies formed from antibody fragments. In certain aspects, the antibody fragment is a scFv.

In other aspects, the binding domain can be an antibody-like molecule, for example, a human domain antibody (dAb), Dual-Affinity Re-Targeting (DART) molecule, a diabody, a di-diabody, dual-variable domain antibody, a Stacked Variable Domain antibody, a Small Modular Immuno Pharmaceutical (SMIP), a Surrobody, a strand-exchange engineered domain (SEED)-body, or TandAb.

The binding domain can be introduced into the native J-chain sequence at any location that allows the binding of the binding domain to its binding target without interfering with the binding of a recipient IgM molecule to its binding target or binding targets or the ability of the J-chain to effectively incorporate into an IgM pentamer. In certain aspects the binding domain can be inserted at or near the C-terminus, at or near the mature N-terminus (e.g., amino acid number 23 of SEQ ID NO: 7 following cleavage of the signal peptide) or at an internal location that, based on the three-dimensional structure of the J-chain is accessible. In certain aspects, the binding domain can be introduced into the native sequence J-chain without about 10 residues from the C-terminus or without about 10 amino acid residues from the mature N-terminus (amino acid 23) of the human J-chain of SEQ ID NO: 7. In another aspect, the binding domain can be introduced into the native sequence human J-chain of SEQ ID NO: 7 in between cysteine residues 113 and 122 of SEQ ID NO: 7, or at an equivalent location of another native sequence J-chain. In a further aspect, the binding domain can be introduced into a native sequence J-chain, such as a J-chain of SEQ ID NO: 7, at or near a glycosylation site. In certain aspects, the binding domain can be introduced into the native sequence human J-chain of SEQ ID NO: 7 within about 10 amino acid residues from the C-terminus.

Introduction can be accomplished by direct or indirect fusion, i.e. by the combination of the J-chain and binding domain in one polypeptide chain by in-frame combination of their coding nucleotide sequences, with or without a peptide linker. The peptide linker (indirect fusion), if used, can be about 1 to 50, or about 1 to 40, or about 1 to 30, or about 1 to 20, or about 1 to 10, or about 10 to 20 amino acids in length, and can be present at one or both ends of the binding domain to be introduced into the J-chain sequence. In certain aspects, the peptide linker is about 10 to 20, or 10 to 15 amino acids long. In certain aspects the peptide linker is 15 amino acids long. In certain aspects the peptide linker is (GGGGS)$_3$ (SEQ ID NO: 12).

It is also possible to introduce more than one heterologous polypeptide, e.g., more than one binding domain or other moiety, into a J-chain.

The modified J-chain can be produced by well-known techniques of recombinant DNA technology, by expressing a nucleic acid encoding the modified J-chain in a suitable prokaryotic or eukaryotic host organism.

The modified J-chain can also be co-expressed with the heavy and light chains of a recipient modified human IgM antibody as described elsewhere herein. The recipient antibody, prior to modified J-chain incorporation, can be monospecific, bispecific or multi-specific, e.g., a monospecific, bispecific, or multispecific modified human IgM antibody. Bispecific and multi-specific IgM antibodies, including antibodies, are described, for example, in PCT Publication Nos. WO 2015/053887, and WO 2015/120474, the entire contents of which are hereby expressly incorporated by reference.

In certain aspects, a modified human IgM antibody as described herein can include a modified J-chain with binding specificity for an immune effector cell, such as a T-cell, NK-cell, a macrophage, or a neutrophil. In certain aspects the effector cell is a T-cell and the binding target is CD3 (discussed below). By activating and redirecting effector cells, e.g. effector T-cells such as cytotoxic T-cells (CTLs), to a cell expressing a target antigen of interest, a modified human IgM antibody as provided herein can produce an enhanced effector response against the target antigen, thereby further increasing potency and efficacy. In certain aspects, the ability of a bispecific modified human IgM antibody as provided herein to elicit T-cell mediated cytotoxicity through binding to CD3 via a modified J-chain is unaffected by the modifications in the IgM constant region that reduce CDC relative to a corresponding wild-type IgM antibody.

In the case of T-cells, cluster of differentiation 3 (CD3) is a multimeric protein complex, known historically as the T3 complex, and is composed of four distinct polypeptide chains (ε, γ, δ, ζ) that assemble and function as three pairs of dimers (εγ, εδ, ζζ). The CD3 complex serves as a T-cell co-receptor that associates non-covalently with the T-cell receptor (TCR). Components of this CD3 complex, especially CD3ε, can be targets for a modified J-chain of a bispecific IgM or IgA binding molecule provided herein.

In certain aspects, a bispecific modified human IgM antibody is provided where the J-chain is modified to bind to CD3ε.

In certain aspects the anti-CD3ε binding domain of a modified J-chain provided herein is a scFv. The anti CD3ε scFv can be fused at or near the N-terminus of the J-chain, or at or near the C-terminus of the J-chain either directly or indirectly with a synthetic linker introduced in between the scFv and the J-chain sequences, e.g., a (GGGGS)$_3$ linker (SEQ ID NO: 12). In certain aspects the scFv comprises the VH and VL regions of visilizumab (Nuvion). In certain aspects the modified J-chain comprises a scFv comprising the VH of visilizumab, a (GGGGS)$_3$ linker (SEQ ID NO: 12), and the VL of visilizumab.

In certain aspects the modified J-chain comprises a scFv of visilizumab fused to the N-terminus of the human J-chain through a 15-amino acid (GGGGS)$_3$ linker (SEQ ID NO: 12), a modified J-chain referred to herein as V15J. V15J can further include a signal peptide to facilitate transport and assembly into a modified human IgM antibody as provided herein. The mature V15J protein is presented as SEQ ID NO: 9, the precursor version, comprising a 19-amino acid-immunoglobulin heavy chain signal peptide is presented as SEQ ID NO: 8. In certain aspects the modified J-chain comprises a scFv of visilizumab fused to the C-terminus of the human J-chain through a 15-amino acid (GGGGS)$_3$ linker (SEQ ID NO: 12), a modified J-chain referred to herein as J15V. J15V can further include a signal peptide to facilitate transport and assembly into a modified human IgM antibody as provided herein. The mature J15V protein is presented as SEQ ID NO: 11, the precursor version, comprising the 22-amino acid-human J-chain signal peptide is presented as SEQ ID NO: 10. In certain aspects, other signal peptides can be used. Selection and inclusion of suitable signal peptides to facilitate expression, secretion, and incorporation of a modified J-chain into a modified human IgM antibody as provided herein is well within the capabilities of a person of ordinary skill in the art.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, N.Y.); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., N.Y.).

Standard reference works setting forth general principles of immunology include Current Protocols in Immunology, John Wiley & Sons, New York; Klein (1982) J., Immunology: The Science of Self-Nonself Discrimination (John Wiley & Sons, N.Y.); Kennett et al., eds. (1980) Monoclonal Antibodies, Hybridoma: A New Dimension in Biological Analyses (Plenum Press, N.Y.); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; W.H. Freeman and Co., N.Y.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All the references cited above, as well as all references cited herein, are incorporated herein by reference in their entireties.

The following examples are offered by way of illustration and not by way of limitation.

EXAMPLES

Example 1: Effects of Cμ3 Domain Mutations on IgM Assembly

Plasmid variants of pFUSEss-CHIg-hM*03-encoding modified human IgM constant regions with single site mutations in the Cμ3 domain, P311A (SEQ ID NO: 2), P313S (SEQ ID NO: 3), both P311A and P313S (SEQ ID NO: 4), D294G (SEQ ID NO: 5), and S283N (SEQ ID NO: 6), were designed and submitted to a commercial vendor for synthesis. Exemplary plasmid constructs that can express wild-type or modified human pentameric or hexameric IgM antibodies comprising the wild-type or modified IgM constant regions, and that can specifically bind to CD20, were produced by the following method.

DNA fragments encoding the VH and VL regions of 1.5.3 (SEQ ID NOs 13 and 14, respectively) were synthesized by a commercial vendor (Genescript), with an EcoRV restriction site on the '5 end and an XbaI restriction site on the 3' end for subcloning into heavy chain and light chain expression vectors. The synthesized DNA constructs were resuspended in Tris-EDTA buffer at 1 µg/ml. DNA samples (1 µg) were digested with EcoRV and XbaI, and the synthesized VH and VL were separated from the carrier plasmid DNA by electrophoresis. The digested DNA was ligated to pre-digested plasmid DNA (pFUSEss-CHIg-hM*03 available from Invivogen or the modified constructs described above for p chain, pFUSE2ss-CLIg-hk for kappa chain, available from Invivogen) by standard molecular biology techniques. The ligated DNAs were transformed into competent bacteria and plated on LB plates with multiple selective antibiotics. Several bacterial colonies were picked, and DNA preparations were made by standard molecular biology techniques. The constructs encoding the heavy chain and light chains were verified by sequencing.

The plasmid constructs encoding the IgM heavy chains and light chains, or the heavy chains, light chains, and J-chain were cotransfected into CHO cells, and cells that express wild-type or modified CD20 IgM antibodies, either with or without J-chain, were selected, all according to standard methods.

Figure 5:
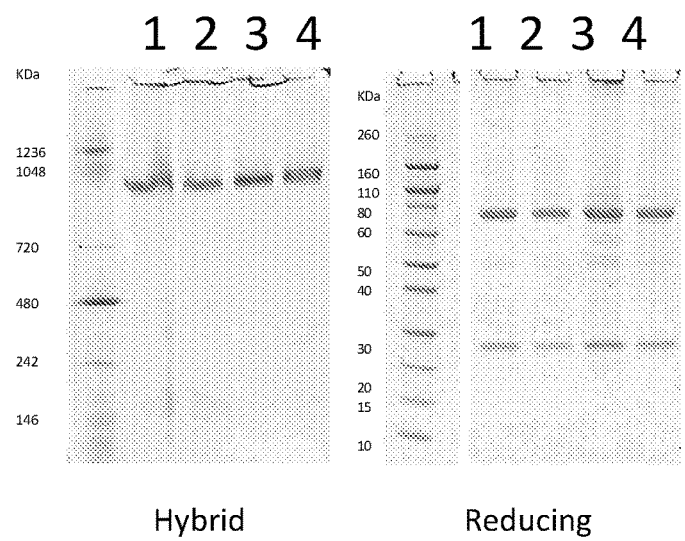
FIG. 5 shows hybrid and reducing gels for 1.5.3 IgM× V15J, and the corresponding 1.5.3×V15J IgM mutants, P311A, P313S, and the double mutant P311A/P313S. The double mutant is expressed and assembled as well as each of the single mutants.

Antibodies present in the cell supernatants were recovered using Capture Select IgM (Catalog 2890.05, BAC, Thermo Fisher) according to the manufacturer's protocol. Antibodies were evaluated on SDS PAGE under non-reducing conditions to show assembly as previously described, e.g., in PCT Publication No. WO 2016/141303 (FIG. 1 and FIG. 5), or under reducing conditions for certain bispecific antibodies (FIG. 5).

Control antibodies (IgM (pure), IgM+J (pure) (an IgM antibody with wild-type J chain) and IgM (an IgM lacking a J chain)) and the IgM Cµ3 domain mutants, S283N, P313S, P311A, and D294G, were evaluated on SDS PAGE under non-reducing conditions to show assembly of the antibodies. NuPage LDS Sample Buffer (Life Technologies) was added to samples before loading onto a NativePage Novex 3-12% bis-Tris Gel (Life Technologies Catalog #BN1003). Novex Tris-Acetate SDS Running Buffer (Life Technologies Catalog #LA0041) was used for gel electrophoresis. The gel was run until the dye front reached the bottom of the gel. After electrophoresis, the gel was stained with Colloidal Blue Stain (Life Technologies Catalog #LC6025).

Figure 1:
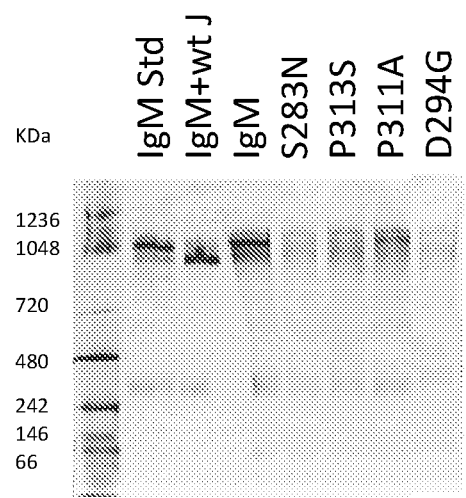

The results, shown in FIG. 1, demonstrate that the IgM Cµ3 domain mutant antibodies assemble as well as control antibodies.

Control bispecific antibody (1.5.3 IgM V15J) and the 1.5.3 IgM V15J Cµ3 domain mutants, P313S, P311A, and the P311A/P313S double mutant, were evaluated on SDS PAGE under non-reducing ("hybrid") and reducing conditions to show assembly of the antibodies. NuPage LDS Sample Buffer (Life Technologies) was added to samples before loading onto a NativePage Novex 3-12% bis-Tris Gel (Life Technologies Catalog #BN1003). Novex Tris-Acetate SDS Running Buffer (Life Technologies Catalog #LA0041) was used for gel electrophoresis. The gel was run until the dye front reached the bottom of the gel. After electrophoresis, the gel was stained with Colloidal Blue Stain (Life Technologies Catalog #LC6025).

The results, shown in FIG. 5, demonstrate that the bispecific IgM Cµ3 domain mutant antibodies assemble as well as control antibody.

Example 2: Complement Dependent Cytotoxicity Activity of IgM Cµ3 Mutants

The CD20-expressing Ramos (ATCC cat. #CRL-1596), cell line was obtained from ATCC and DSMZ. 50,000 cells were seeded in a 96-well plate. Cells were treated with the wild-type control antibodies, 1.5.3 IgM, 1.5.3 IgG and 1.5.3 IgM×V15J, as well as the IgM Cµ3 domain single mutants (P311A, P313S, D294G, and S283N). Human serum complement (Quidel cat. #A113) was added to antibody-treated cells at a final concentration of 10%. The reaction mixtures were incubated at 37° C. for 4 hours. CELLTITER-GLO® reagent (Promega cat. #G7572) was added at a volume equal to the volume of culture medium present in each well. The plate was shaken for 2 minutes, incubated for 10 minutes at room temperature, and luminescence was measured on a luminometer.

Figure 2:
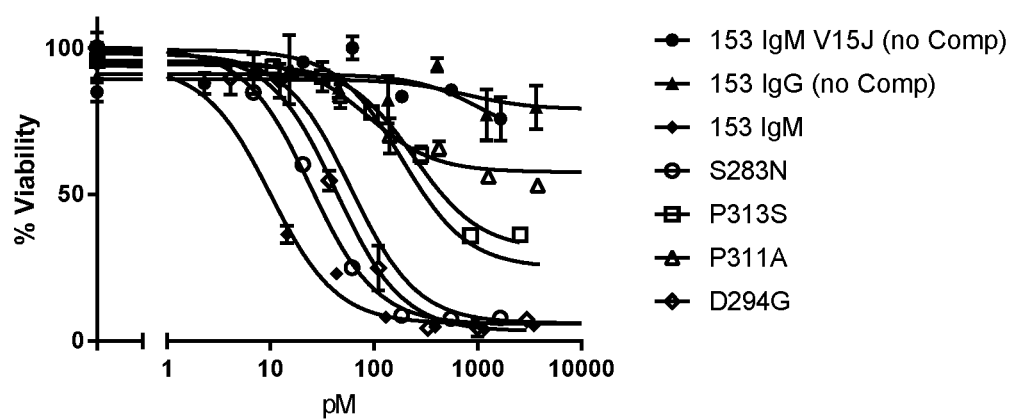

The results are shown in FIG. 2. Two IgM Cµ3 single mutants, P311A and P313S, exhibited approximately 50% less cell killing than the control 1.5.3 IgM antibodies in the presence of complement. IgM Cµ3 mutants, S283N and D294G, showed similar cell killing with complement to the control wild-type IgMs. In the absence of complement, minimal cell killing was observed for the 1.5.3 IgG and 1.5.3 IgM×V15J antibodies.

Example 3: Complement Dependent Cytotoxicity of Bispecific Anti-CD20×Anti-CD3 IgM Cµ3 Mutants The CD20-expressing Ramos (ATCC cat. #CRL-1596), cell line was obtained from ATCC and DSMZ. 50,000 cells were seeded in a 96-well plate. Cells were treated with control antibody, 1.5.3 IgM×V15J, and the bispecific IgM Cµ3 domain mutants (P311A×V15J, P313S×V15J, D294G× V15J, and S283N×V15J). All the antibodies included a J chain bispecific for CD20 and CD3 generated and expressed as previously described, see, PCT Publication No. WO 2016/141303. Human serum complement (Quidel cat. #A113) was added to the antibody-treated cells at a final concentration of 10%. The reaction mixtures were incubated at 37° C. for 4 hours. CELLTITER-GLO® reagent (Promega cat. #G7572) was added at a volume equal to the volume of culture medium present in each well. The plate was shaken for 2 minutes, incubated for 10 minutes at room temperature, and luminescence was measured on a luminometer.

Figure 3:
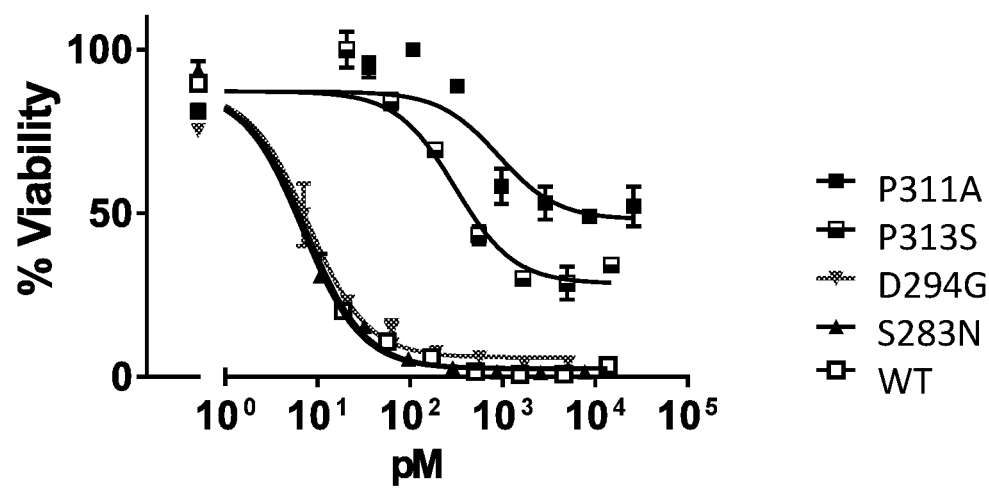
FIG. 3 shows percent CDC activity for anti-CD20×anti-CD3 bispecific IgM antibodies with an anti-CD3 modified J-chain including the control 1.5.3 IgM×V15J antibody, and corresponding 1.5.3 IgM×V15J mutants, P311A, P313S, D294G, and S283N.
Figure 6:
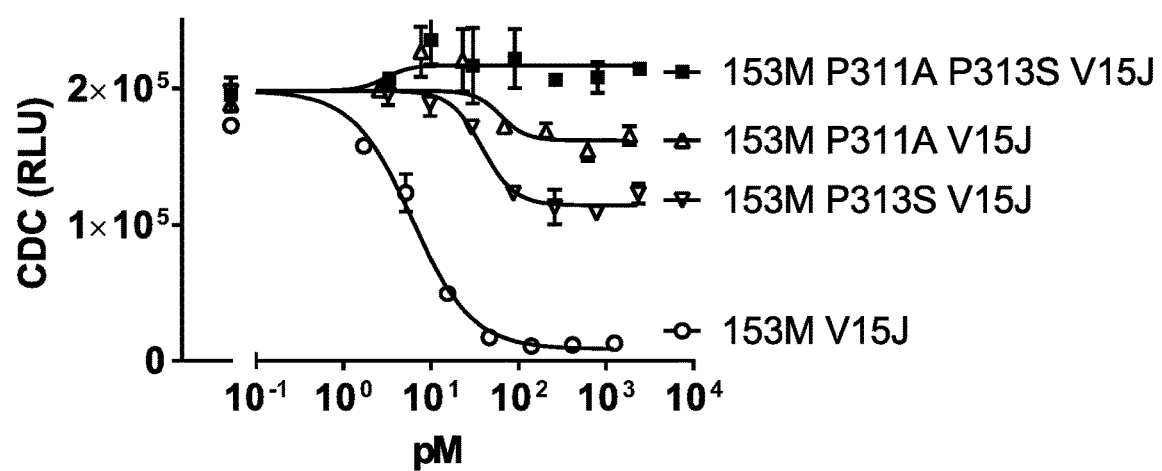
FIG. 6 shows CDC activity for 1.5.3 IgM×V15J, and the corresponding 1.5.3×V15J IgM mutants, P311A, P313S, and the double mutant P311A/P313S. The double mutant shows complete elimination of CDC activity.

The results are shown in FIG. 3 and in FIG. 6. The bispecific IgM Cµ3 mutants, P311A and P313S, exhibited half maximal Ramos cell killing with complement, whereas control 1.5.3 IgM×V15J and the bispecific IgM Cµ3 mutants D294G and S283N achieved nearly maximal complement dependent cytotoxicity (90-100% effective) in the presence of complement. In the assay shown in FIG. 6, bispecific IgM Cµ3 mutant P311A exhibited maximum killing of about 46% with complement ($EC_{50}$ was undefined), while the P313S mutant showed maximum killing of 31% with complement ($EC_{50}$ was 243 µM). Complement-mediated killing was essentially eliminated in the double mutant, P311A/P313S (FIG. 6, see also Table 2).

Example 4: T-Cell Activation Potential of Bispecific Anti-CD20×Anti-CD3 IgM Cµ3 Mutants Engineered Jurkat T-cells (Promega CS176403) and RPM18226 cells (ATCC CCL-155) were cultured in RPMI (Invitrogen) supplemented with 10% Fetal Bovine Serum (Invitrogen). Serial dilutions of bispecific 1.5.3 IgM×V15J antibody and the bispecific IgM Cμ3 mutants, D294G× V15J, S283N×V15J, P313S×V15J, P311A×V15J, P311A/P313S×V15J, and 1.5.3 IgM (without J-chain) were incubated with 7500 RPM18226 cells in 20 μL in a white 384 well assay plate for 2h at 37° C. with 5% $CO_2$. The engineered Jurkat cells (25000) were added to mixture to final volume of 40 μL. The mixture was incubated for 5h at 37° C. with 5% $CO_2$. The cell mixtures were then mixed with 20 μL lysis buffer containing luciferin (Promega, CELLTITER-GLO®) to measure luciferase reporter activity. Light output was measured by EnVision plate reader. $EC_{50}$ was determined by 4 parameter curve fit using Prism software.

Figure 4:
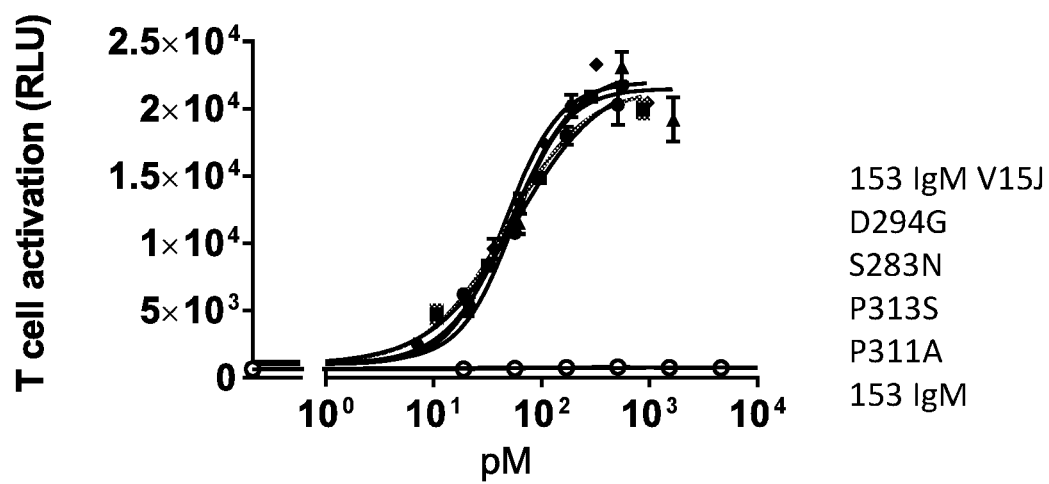
FIG. 4 shows a T cell activation assay for a control anti-CD20 IgM lacking the anti-CD3 modified J-chain, and bispecific IgM antibodies that contain the anti-CD3 modified J-chain (V15J) including the control antibody, 1.5.3 IgM× V15J, and the corresponding 1.5.3×V15J IgM mutants, D294G, S283N, P313S, and P311A.
Figure 7:
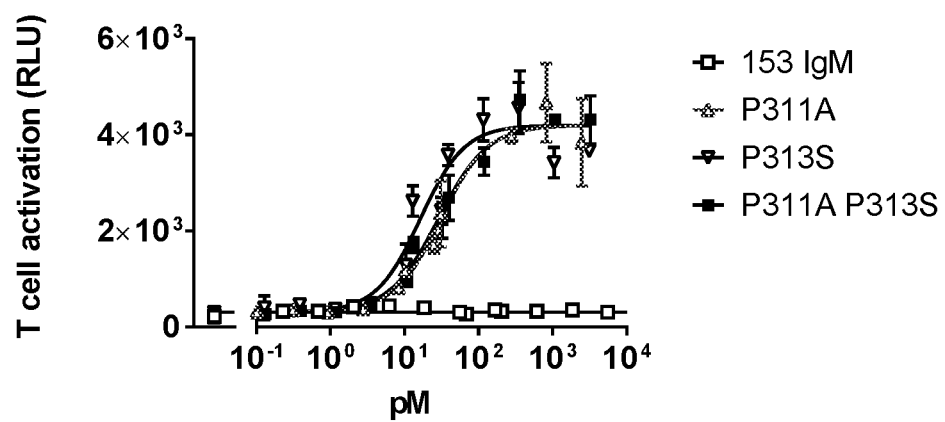
FIG. 7 shows a T cell activation assay for 1.5.3 IgM× V15J, and the corresponding 1.5.3×V15J IgM mutants, P311A, P313S, and the double mutant P311A/P313S. The double mutant is as effective at activating T-cells as each of the single mutants.

The results are shown in FIG. 4 and in FIG. 7. All of the bispecific IgM Cμ3 mutants activated T cells as effectively as the bispecific control antibody (1.5.3 IgM×V15J). No T cell activation was observed in the IgM control lacking the bispecific J chain (1.5.3 IgM).

Example 5: Complement Dependent Cytotoxicity of Additional Bispecific Anti-CD20×Anti-CD3 IgM Cμ3 Mutants To further evaluate the effect of Cμ3 mutations on CDC activity, systematic single amino acid ala substitutions were made at each position from T302 of SEQ ID NO: 1 to K322 of SEQ ID NO: 1. Each of these mutant IgM constant regions were assembled as 1.5.3 IgM V15J Cμ3 domain mutants as described in Example 1, and were tested for CDC activity as described in Example 3 and for T cell activation as described in Example 4. In addition to the previously evaluated mutations at P311 and P313, 1.5.3 IgM V15J Cμ3 domain ala substitutions at L310 (SEQ ID NO: 15) and K315 (SEQ ID NO: 16) modestly reduced CDC activity with an increased $EC_{50}$, as shown in FIG. 8 and Table 2, without significantly affecting T cell activation (data not shown).

Various combinations of double substitutions at two of positions L310, P311, P313, and K315 were also constructed as described in Example 1 and were tested for CDC activity as described in Example 3. These included double mutants L310A, K315A (SEQ ID NO: 17), L310S, K315S (SEQ ID NO: 18), L310A, P311A (SEQ ID NO: 19), L310A, P313S (SEQ ID NO: 20), P311A, K315A (SEQ ID NO: 21), and P313S, K315A (SEQ ID NO: 22). The CDC activity of these double mutants relative to wild-type human IgM is summarized in Table 2. The L310A, K315A double mutant shown an enhanced reduction in CDC activity relative to either of the single mutations.

Additional amino acid substitutions at positions L310 and K315 were evaluated to determine the effect of charged or polar amino acids on CDC activity. L310 was substituted with the negatively-charged aspartic acid (D, SEQ ID NO: 23), and K315 was substituted with aspartic acid (D, SEQ ID NO: 24) or the polar amino acid glutamine (Q, SEQ ID NO: 25). These mutants were tested for CDC activity as described in Example 3. The results are shown in FIG. 9A and FIG. 9B, and in Table 2. The introduction of negatively-charged amino acids at positions 310 or 315 disrupted CDC activity more than the neutral ala substitutions.

TABLE 2

CDC Activity of Human IgM Cμ3 Mutants

| Substitution(s) | SEQ ID NO: | 309 | 310 | 311 | 312 | 313 | 314 | 315 | 316 | Fold $EC_{50}$ Increase | % CDC Relative to Wild Type |
|---|---|---|---|---|---|---|---|---|---|---|---|
| WT | 26 | D | L | P | S | P | L | K | Q | 1 | 100% |
| L310A | 27 | | A | | | | | | | 2 | 95% |
| P311A | 28 | | | A | | | | | | 11 | 46% |
| P313S | 29 | | | | | S | | | | 6 | 83% |
| K315A | 30 | | | | | | | A | | 5 | 95% |
| L310D | 31 | | D | | | | | | | ND | 12% |
| K315D | 32 | | | | | | | D | | 7 | 50% |
| K315Q | 33 | | | | | | | Q | | 3 | 85% |
| L310A K315A | 34 | | A | | | | | A | | 80 | 52% |
| L310S K315S | 35 | | S | | | | | S | | 8 | 86% |
| L310A P311A | 36 | | A | A | | | | | | ND | 18% |
| L310A P313S | 37 | | A | | | S | | | | 6 | 39% |
| P311A K315A | 38 | | | A | | | | A | | 100 | 29% |
| P313S K315A | 39 | | | | | S | | A | | 16 | 47% |
| P311A P313S | 40 | | | A | | S | | | | ND | 25% |

TABLE 3

Sequences

| SEQ ID NO | Short Name | Sequence |
|---|---|---|
| 1 | human IgM constant region AA | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLPSPLKQTISRPKGVALHRPDVYLLPP |

TABLE 3-continued

Sequences

| SEQ ID NO | Short Name | Sequence |
|---|---|---|
| | | AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 2 | Modified human IgM constant region P311A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLASPLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 3 | Modified human IgM constant region P313S | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLPSSLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 4 | Modified human IgM constant region P311A/P313S | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLASSLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 5 | Modified human IgM constant region D294G | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDGWNSGERFTCTVTHTDLPSPLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 6 | Modified human IgM constant region S283N | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFNAVGEA SICEDDWNSGERFTCTVTHTDLPSPLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 7 | J-chain AA | MKNHLLFWGVLAVFIKAVHVKAQEDERIVLVDNKCKCARITSRIIRSS EDPNEDIVERNIIIVPLNNRENISDPTSPLRTRFVYHLSDLCKKCDPT EVELDNQIVTATQSNICDEDSATETCYTDRNKCYTAVVPLVYGGETK MVETALTPDACYPD |
| 8 | precursor modified J-chain sequence for V15J | MGWSYIILFLVATATGVHSQVQLVQSGAEVKKPGASVKVSCKASGYTF ISYTMHWVRQAPGQGLEWMGYINPRSGYTHYNQKLKDKATLTADKSAS TAYMELSSLRSEDTAVYYCARSAYYDYDGFAYWGQGTLVTVSSGGGGS GGGGSGGGGSDIQMTQSPSSLSASVGDRVTITCSASSSVSYMNWYQQK PGKAPKRLIYDTSKLASGVPSRFSGSGSGTDFTLTISSLQPEDFATYY CQQWSSNPPTFGGGTKLEIKGGGGSGGGGSGGGGSQEDERIVLVDNKC KCARITSRIIRSSEDPNEDIVERNIRIIVPLNNRENISDPTSPLRTRF VYHLSDLCKKCDPTEVELDNQIVTATQSNICDEDSATETCYTDRNKC YTAVVPLVYGGETKMVETALTPDACYPD |
| 9 | mature modified | QVQLVQSGAEVKKPGASVKVSCKASGYTFISYTMHWVRQAPGQGLEWM GYINPRSGYTHYNQKLKDKATLTADKSASTAYMELSSLRSEDTAVYYC |

TABLE 3-continued

Sequences

| SEQ ID NO | Short Name | Sequence |
|---|---|---|
| | J-chain sequence for V15J | ARSAYYDYDGFAYWGQGTLVTVSSGGGGSGGGGSGGGGSDIQMTQSPS SLSASVGDRVTITCSASSSVSYMNWYQQKPGKAPKRLIYDTSKLASGV PSRFSGSGSGTDFTLTISSLQPEDFATYYCQQWSSNPPTFGGGTKLEI KGGGGSGGGGSGGGGSQEDERIVLVDNKCKCARITSRIIRSSEDPNED IVERNIRIIVPLNNRENISDPTSPLRTRFVYHLSDLCKKCDPTEVELD NQIVTATQSNICDEDSATETCYTYDRNKCYTAVVPLVYGGETKMVETA LTPDACYPD |
| 10 | Precursor modified J-chain sequence for J15V | MKNHLLFWGVLAVFIKAVHVKAQEDERIVLVDNKCKCARITSRIIRSS EDPNEDIVERNIRIIVPLNNRENISDPTSPLRTRFVYHLSDLCKKCDP TEVELDNQIVTATQSNICDEDSATETCYTYDRNKCYTAVVPLVYGGET KMVETALTPDACYPDGGGGSGGGGSGGGGSQVQLVQSGAEVKKPGASV KVSCKASGYTFISYTMHWVRQAPGQGLEWMGYINPRSGYTHYNQKLKD KATLTADKSASTAYMELSSLRSEDTAVYYCARSAYYDYDGFAYWGQGT LVTVSSGGGGSGGGGSGGGGSDIQMTQSPSSLSASVGDRVTITCSASS SVSYMNWYQQKPGKAPKRLIYDTSKLASGVPSRFSGSGSGTDFTLTIS SLQPEDFATYYCQQWSSNPPTFGGGTKLEIK |
| 11 | mature modified J-chain sequence for J15V | QEDERIVLVDNKCKCARITSRIIRSSEDPNEDIVERNIRIIVPLNNRE NISDPTSPLRTRFVYHLSDLCKKCDPTEVELDNQIVTATQSNICDEDS ATETCYTYDRNKCYTAVVPLVYGGETKMVETALTPDACYPDGGGGSGG GGSGGGGSQVQLVQSGAEVKKPGASVKVSCKASGYTFISYTMHWVRQA PGQGLEWMGYINPRSGYTHYNQKLKDKATLTADKSASTAYMELSSLRS EDTAVYYCARSAYYDYDGFAYWGQGTLVTVSSGGGGSGGGGSGGGGSD IQMTQSPSSLSASVGDRVTITCSASSSVSYMNWYQQKPGKAPKRLIYD TSKLASGVPSRFSGSGSGTDFTLTISSLQPEDFATYYCQQWSSNPPTF GGGTKLEIK |
| 12 | (GGGGS)₃ linker | GGGGSGGGGSGGGGS |
| 13 | 1.5.3 VH | EVQLVQSGAEVKKPGESLKISCKGSGYSFTSYWIGW VRQMPGKGLEWMGIIYPGDSDTRYSPSFQGQVTISADKSITTAYLQWS SLKASDTAMYYCARHPSYGSGSPNFDYWGQGTLVTVSS |
| 14 | 1.5.3 VL | DIVMTQTPLSSPVTLGQPASISCRSSQSLVYSDGNTYLSWLQQRPGQP PRLLIYKISNRFSGVPDRFSGSGAGTDFTLKISRVEAEDVGVYYCVQA TQFPLTFGGGTKVEIK |
| 15 | Modified human IgM constant region L310A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDAPSPLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 16 | Modified human IgM constant region K315A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLPSPLAQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 17 | Modified human IgM constant region L310A, K315A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDAPSPLAQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 18 | Modified human IgM constant region | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ |

TABLE 3-continued

Sequences

| SEQ ID NO | Short Name | Sequence |
|---|---|---|
| | L310S, K315S | SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDSPSPLSQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 19 | Modified human IgM constant region L310A, P311A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDAASPLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 20 | Modified human IgM constant region L310A, P313A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDAPSSLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 21 | Modified human IgM constant region P311A, K315A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLASPLAQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 22 | Modified human IgM constant region P313S, K315A | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLPSSLAQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 23 | Modified human IgM constant region L310D | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDDPSPLKQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 24 | Modified human IgM constant region K315D | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLPSPLDQTISRPKGVALHRPDVYLLPP AREQLNLRESATITCLVTGFSPADVFVQWMQRGQPLSPEKYVTSAPMP EPQAPGRYFAHSILTVSEEEWNTGETYTCVVAHEALPNRVTERTVDKS TGKPTLYNVSLVMSDTAGTCY |
| 25 | Modified human IgM constant | GSASAPTLFPLVSCENSPSDTSSVAVGCLAQDFLPDSITFSWKYKNNS DISSTRGFPSVLRGGKYAATSQVLLPSKDVMQGTDEHVVCKVQHPNGN KEKNVPLPVIAELPPKVSVFVPPRDGFFGNPRKSKLICQATGFSPRQI |

TABLE 3-continued

Sequences

| SEQ ID NO | Short Name | Sequence |
|---|---|---|
| | region K315Q | QVSWLREGKQVGSGVTTDQVQAEAKESGPTTYKVTSTLTIKESDWLSQ SMFTCRVDHRGLTFQQNASSMCVPDQDTAIRVFAIPPSFASIFLTKST KLTCLVTDLTTYDSVTISWTRQNGEAVKTHTNISESHPNATFSAVGEA SICEDDWNSGERFTCTVTHTDLPSPLQQTISRPKGVALHRPDVYLLPP AREQLNLRESATITCLVTGFSPADVFVQWMRGQPLSPEKYVTSAPMP EPQAPGRYFAHSILTVSEEEWNTGETYTCVVAHEALPNRVTERTVDKS TGKPTLYNVSLVMSDTAGTCY |

The breadth and scope of the present disclosure should not be limited by any of the above-described exemplary embodiments but should be defined only in accordance with the following claims and their equivalents.

What is claimed is:

1. A modified human IgM constant region comprising one or more amino acid substitutions relative to a wild-type human IgM constant region, wherein at least one amino acid substitution is in the Cμ3 domain at position L310 of SEQ ID NO: 1, position P311 of SEQ ID NO: 1, position P313 of SEQ ID NO: 1, position K315 of SEQ ID NO: 1, or a combination thereof, and wherein a modified IgM antibody comprising the modified IgM constant region and a heavy chain variable region specific for a target antigen exhibits reduced complement-dependent cytotoxicity (CDC) of cells expressing the target antigen relative to a corresponding wild-type human IgM antibody identical except for the modified human IgM.

2. The modified human IgM constant region of claim 1, wherein the amino acid substitution is at position L310 of SEQ ID NO: 1, and wherein L310 of SEQ ID NO: 1 is substituted with alanine (L310A), serine (L310S), aspartic acid (L310D) or glycine (L310G).

3. The modified human IgM constant region of claim 1, wherein the amino acid substitution is at position P311 of SEQ ID NO: 1, and wherein P311 of SEQ ID NO: 1 is substituted with alanine (P311A), serine (P311S), or glycine (P311G).

4. The modified human IgM constant region of claim 1, wherein the amino acid substitution is at position P313 of SEQ ID NO: 1, and wherein P313 of SEQ ID NO: 1 is substituted with alanine (P313A), serine (P313S), or glycine (P313G).

5. The modified human IgM constant region of claim 1, wherein the amino acid substitution is at position K315 of SEQ ID NO: 1, and wherein K315 of SEQ ID NO: 1 is substituted with alanine (K315A), serine (K315S), aspartic acid (K315D), glutamine (K315Q), or glycine (K315G).

6. The modified human IgM constant region of claim 5, wherein K315 of SEQ ID NO: 1 is substituted with aspartic acid (K315D).

7. The modified human IgM constant region of claim 1, comprising amino acid substitutions at positions P311 and P313 of SEQ ID NO: 1, wherein P311 of SEQ ID NO: 1 is substituted with alanine (P311A), serine (P311S), or glycine (P311G), and wherein P313 of SEQ ID NO: 1 is substituted with alanine (P313A), serine (P313S), or glycine (P313G).

8. The modified human IgM constant region of claim 7, wherein P311 of SEQ ID NO: 1 is substituted with alanine (P311A) and P313 of SEQ ID NO: 1 is substituted with serine (P313S).

9. The modified human IgM constant region of claim 1, comprising
(a) amino acid substitutions at positions L310 and K315 of SEQ ID NO: 1, wherein L310 is substituted with alanine (L310A) or serine (L310S) and K315 is substituted with alanine (K315A) or serine (K315S);
(b) amino acid substitutions at positions L310 and P311 of SEQ ID NO: 1, wherein L310 is substituted with alanine (L310A) and P311 is substituted with alanine (P311A);
(c) amino acid substitutions at positions L310 and P313 of SEQ ID NO: 1, wherein L310 is substituted with alanine (L310A) and P313 is substituted with serine (P313S);
(d) amino acid substitutions at positions P311 and K315 of SEQ ID NO: 1, wherein P311 is substituted with alanine (P311A) and K315 is substituted with alanine (K315A); or
(e) amino acid substitutions at positions P313 and K315 of SEQ ID NO: 1, wherein P313 is substituted with serine (P313S) and K315 is substituted with alanine (K315A).

10. The modified human IgM constant region of claim 1, comprising SEQ ID NO: 2, SEQ ID NO: 3, SEQ ID NO: 15, SEQ ID NO: 16, SEQ ID NO: 24, SEQ ID NO: 25, SEQ ID NO: 4, SEQ ID NO: 17, SEQ ID NO: 18, SEQ ID NO: 19, SEQ ID NO: 20, SEQ ID NO: 21, SEQ ID NO: 22 or SEQ ID NO: 23.

11. The modified human IgM constant region of claim 10, wherein the maximum CDC activity achieved by a target-specific IgM antibody comprising the modified human IgM constant region in a dose-response assay is reduced by at least 5%, 10%, 20%, 30%, 40%, 50%, 60%, 70%, 80%, 90%, 95%, or 100% relative to a corresponding wild-type IgM antibody identical except for the modified human IgM constant region.

12. A modified human IgM antibody comprising the modified human IgM constant region of claim 1, and a heavy chain variable region (VH) situated amino terminal to the modified human IgM constant region, wherein the modified human IgM antibody specifically binds to a target antigen and exhibits reduced complement-dependent cytotoxicity (CDC) of cells expressing the target antigen relative to a corresponding wild-type human IgM antibody.

13. The modified human IgM antibody of claim 12, which is a pentameric or a hexameric antibody comprising five or six bivalent IgM binding units, respectively, wherein each binding unit comprises two IgM heavy chains each comprising a VH situated amino terminal to the modified human IgM constant region, and two immunoglobulin light chains each comprising a light chain variable domain (VL) situated amino terminal to a human immunoglobulin light chain constant region.

14. The modified human IgM antibody of claim 13, which is a pentameric antibody, and further comprises a J-chain or a functional variant thereof.

15. The modified human IgM antibody of claim 14, wherein the J-chain or variant thereof is a modified J-chain further comprising a heterologous polypeptide, wherein the heterologous polypeptide is directly or indirectly fused to the J-chain or variant thereof.

16. The modified human IgM antibody of claim 15, wherein the heterologous polypeptide is fused to the J-chain or variant thereof via a peptide linker to the N-terminus of the J-chain or variant thereof, the C-terminus of the J-chain or variant thereof, or to both the N-terminus and C-terminus of the J-chain or variant thereof, wherein the peptide linker comprises at least 5 amino acids, but no more than 25 amino acids.

17. The modified human IgM antibody of claim 16, wherein the heterologous polypeptide comprises an antibody or antigen-binding fragment thereof.

18. The modified human IgM antibody of claim 17, wherein the antigen-binding fragment is a scFv.

19. The modified human IgM antibody of claim 18, wherein the heterologous polypeptide can specifically bind to CD3ε.

20. A polynucleotide comprising a nucleic acid sequence that encodes the modified human IgM antibody of claim 1.

21. A composition comprising a first polynucleotide comprising a nucleic acid sequence that encodes the VH and the modified human IgM constant region of the modified human IgM antibody of claim 12 and a second polynucleotide comprising a nucleic acid sequence that encodes a light chain polypeptide comprising a human antibody light chain constant region fused to the C-terminal end of a light chain variable domain (VL).

22. The composition of claim 21, further comprising a nucleic acid sequence that encodes a J-chain or a functional variant thereof.

23. A host cell comprising the composition of claim 21.

24. A method of producing the modified human IgM antibody, comprising culturing the host cell of claim 23, and recovering the modified human IgM antibody.

25. The modified human IgM constant region of claim 3, wherein P311 of SEQ ID NO: 1 is substituted with alanine (P311A).

26. The modified human IgM constant region of claim 25, comprising SEQ ID NO: 2.

27. The modified human IgM constant region of claim 4, wherein P313 of SEQ ID NO: 1 is substituted with serine (P313S).

28. The modified human IgM constant region of claim 27, comprising SEQ ID NO: 3.

29. The modified human IgM constant region of claim 8, comprising SEQ ID NO: 4.

30. The modified human IgM constant region of claim 6, comprising SEQ ID NO: 24.

31. The modified human IgM antibody of claim 12, wherein the modified human IgM constant region comprises SEQ ID NO: 2, SEQ ID NO: 3, SEQ ID NO: 15, SEQ ID NO: 16, SEQ ID NO: 24, SEQ ID NO: 25, SEQ ID NO: 4, SEQ ID NO: 17, SEQ ID NO: 18, SEQ ID NO: 19, SEQ ID NO: 20, SEQ ID NO: 21, SEQ ID NO: 22, or SEQ ID NO: 23.

32. The modified human IgM antibody of claim 31, wherein the modified human IgM constant region comprises SEQ ID NO: 4.

33. The modified human IgM antibody of claim 31, wherein the modified human IgM constant region comprises SEQ ID NO: 24.

34. The modified human IgM antibody of claim 13, wherein the modified human IgM constant region comprises SEQ ID NO: 2, SEQ ID NO: 3, SEQ ID NO: 15, SEQ ID NO: 16, SEQ ID NO: 24, SEQ ID NO: 25, SEQ ID NO: 4, SEQ ID NO: 17, SEQ ID NO: 18, SEQ ID NO: 19, SEQ ID NO: 20, SEQ ID NO: 21, SEQ ID NO: 22 or SEQ ID NO: 23.

35. The modified human IgM antibody of claim 34, wherein the modified human IgM constant region comprises SEQ ID NO: 4.

36. The modified human IgM antibody of claim 34, wherein the modified human IgM constant region comprises SEQ ID NO: 24.

\* \* \* \* \*

UNITED STATES PATENT AND TRADEMARK OFFICE
CERTIFICATE OF CORRECTION

| | |
|---|---|
| PATENT NO. | : 11,401,337 B2 |
| APPLICATION NO. | : 16/500292 |
| DATED | : August 2, 2022 |
| INVENTOR(S) | : Ramesh Baliga and Dean Ng |

It is certified that error appears in the above-identified patent and that said Letters Patent is hereby corrected as shown below:

In the Claims

Column 100, Line 62, Claim 20, replace "human IgM antibody of claim 1." with --human IgM constant region of claim 1.--

Signed and Sealed this
Twelfth Day of September, 2023

Katherine Kelly Vidal
*Director of the United States Patent and Trademark Office*